United States Patent [19]
Sasabe et al.

[11] Patent Number: 5,986,750
[45] Date of Patent: Nov. 16, 1999

[54] METHOD AND AN APPARATUS FOR MEASURING THE INCLINATION ANGLE OF A PILE OF A POWDERY OR GRANULAR MATERIAL

[75] Inventors: Shuji Sasabe, Yawata; Yoshiyuki Inoue, Kyoto; Kenji Takebayashi, Yawata; Toyokazu Yokoyama, Kuse-Gun; Tadami Hanakawa, Habikino, all of Japan

[73] Assignee: Hosokawa Micron Corporation, Osaka, Japan

[21] Appl. No.: 09/103,552

[22] Filed: Jun. 24, 1998

[30] Foreign Application Priority Data

Jun. 25, 1997 [JP] Japan .................................. 9-168286
Dec. 1, 1997 [JP] Japan .................................. 9-329765

[51] Int. Cl.$^6$ .......................... G01B 11/26; G01B 11/24; G01F 11/28
[52] U.S. Cl. .................................. 356/152.1; 356/139.3; 356/376; 702/167; 222/437
[58] Field of Search .......................... 356/139.03, 152.1, 356/376, 139.1; 702/167; 222/437

[56] References Cited

U.S. PATENT DOCUMENTS

| | | |
|---|---|---|
| 4,041,476 | 8/1977 | Swainson . |
| 4,905,512 | 3/1990 | Hayashi . |
| 5,335,547 | 8/1994 | Nakajima et al. . |
| 5,377,011 | 12/1994 | Koch ........................................ 356/376 |

*Primary Examiner*—Stephen C. Buczinski
*Attorney, Agent, or Firm*—McDermott, Will, Emery

[57] ABSTRACT

By the side of a powdery or granular material stacked in a conical pile on a horizontal surface, a sensor that emits sensor light and, by receiving light reflected from a spot illuminated by the sensor light, detects the distance to the pile of the powdery or granular material is placed with the optical axis of the sensor light horizontal. While the sensor is moved in a horizontal direction perpendicular to the optical axis of the sensor light, the distance to each of a plurality of measurement points arranged horizontally at regular intervals along a line that runs on said pile of the powdery or granular material so as to face the movement path of the sensor. This step is performed every time the sensor is moved vertically a predetermined distance at a time. In each session of the step, a point is extracted that is closest to the sensor, and a function describing a straight line approximating the curve through all of the thus extracted points is determined by the least-squares method. Then, the angle of this straight line with respect to a horizontal plane is determined.

19 Claims, 21 Drawing Sheets

METHOD AND AN APPARATUS FOR MEASURING THE INCLINATION ANGLE OF A PILE OF A POWDERY OR GRANULAR MATERIAL

BACKGROUND OF THE INVENTION

1. Field of the Invention

The present invention relates to a method and an apparatus for measuring the inclination angle of the free surface of a powdery or granular material stacked in a pile.

2. Description of the Prior Art

In general, in planning and designing a process for treating a powdery or granular material, in quality control of a powdery or granular material, or in a similar operation, it is essential to have a clear grasp of the flow and jet characteristics of the powdery or granular material treated. These characteristics are evaluated on the basis of various property values, such as the angle of repose and the spatula angle, that the powdery or granular material exhibits when it is stacked in a pile. Conventionally, the angle of repose and the spatula angle are measured by putting a protractor on the free surface of a pile of a powdery or granular material and reading the scale on the protractor.

However, in the measurement method described above, the protractor can be put in more than one way when the free surface of the pile of the powdery or granular material is uneven. This means that measurement results reflect how a measurer habitually conducts and evaluates the measurement, and therefore that different measurers often obtain different measurement results from the same measurement sample. In addition, determining the appropriate manner of putting the protractor is time-consuming, and thus the measurement as a whole requires an unduly long time.

SUMMARY OF THE INVENTION

An object of the present invention is, in the measurement of the inclination angle of the free surface of a powdery or granular material stacked in a pile, to eliminate the variations that appear in measurement results depending on how a measurer conducts the measurement, and to reduce the time and effort required to conduct the measurement.

To achieve the above object, according to one aspect of the present invention, a method of measuring the inclination angle of a pile of a powdery or granular material includes: a first step of placing, by the side of a conical pile of the powdery or granular material stacked on a horizontal surface, a sensor that emits sensor light and, by receiving the light reflected from a spot illuminated by the sensor light, measures the distance to that spot, the sensor being placed in such a way that an opening through which the sensor light is emitted faces a free surface of the pile of the powdery or granular material and that the optical axis of the sensor light runs in a horizontal direction; a second step of moving the sensor in a horizontal direction perpendicular to the optical axis to detect the distance to each of a plurality of measurement points along a line that runs on the free surface so as to face the movement path of the sensor, the measurement points being arranged along the line at regular intervals in a horizontal direction, starting at one end and ending at the other end of the line in a horizontal direction; a third step of moving the sensor in a vertical direction a predetermined distance at a time and performing the second step every time the sensor is so moved; a fourth step of extracting a measurement point that is closest to the sensor in each session of the second step and determining the function describing a straight line approximating the curve through all of the thus extracted measurement points by the least-squares method; and a fifth step of determining the inclination angle of the straight line determined in the forth step with respect to a horizontal plane.

According to another aspect of the present invention, a method of measuring the inclination angle of a pile of a powdery or granular material includes: a first step of placing, above a conical pile of the powdery or granular material stacked on a horizontal surface, a sensor that emits sensor light and, by receiving the light reflected from a spot illuminated by the sensor light, measures the distance to that spot, the sensor being placed in such a way that an opening through which the sensor light is emitted faces a free surface of the pile of the powdery or granular material and that the optical axis of the sensor light runs in a vertical direction; a second step of moving the sensor in a horizontal direction within a vertical plane including the vertex of the pile of the powdery or granular material to detect the distance to each of a plurality of measurement points along a ridge line of the pile of the powdery or granular material, the measurement points being arranged along the ridge line at regular intervals in a horizontal direction; a third step of determining the function describing a straight line approximating the curve through the plurality of measurement points by the least-squares method; and a fourth step of determining the inclination angle of the straight line determined in the third step with respect to a horizontal plane.

According to another aspect of the present invention, a method of measuring the inclination angle of a pile of a powdery or granular material includes: a first step of placing, by the side of a pile of the powdery or granular material stacked on a spatula supported horizontally, a sensor that emits sensor light and, by receiving the light reflected from a spot illuminated by the sensor light, measures the distance to that spot, the sensor being placed in such a way that an opening through which the sensor light is emitted faces a free surface of the pile of the powdery or granular material and that the optical axis of the sensor light runs in a horizontal direction; a second step of moving the sensor in a vertical direction to detect the distance to each of a plurality of measurement points along a line that runs on the free surface so as to face the movement path of the sensor, the measurement points being arranged along the line at regular intervals in a vertical direction; a third step of determining the function describing a straight line approximating the curve through the plurality of measurement points by the least-squares method; and a fourth step of determining the angle of the straight line determined in the third step with respect to a horizontal plane.

According to another aspect of the present invention, an apparatus for measuring the inclination angle of a pile of a powdery or granular material is provided with: a horizontal surface on which the powdery or granular material is stacked in a pile; a sensor, placed by the side of the powdery or granular material stacked in a conical pile on the horizontal surface, that emits sensor light in a horizontal direction toward a free surface of the pile of the powdery or granular material and, by receiving the light reflected from a spot illuminated by the sensor light, detects the distance to that spot; a moving means for moving the sensor in horizontal and vertical directions perpendicular to the optical axis of the sensor light; and a control means for controlling the moving means and for processing the data obtained from the sensor. In this apparatus, the sensor is moved in a vertical direction a predetermined distance at a time and, every time the sensor is so moved, a step is performed in which the sensor is moved in a horizontal direction to detect the distance to each of a plurality of measurement points along a line that runs on the free surface of the pile of the powdery or granular material so as to face the movement path of the sensor, with the measurement points arranged along the line at regular intervals in a horizontal direction, starting at one end and ending at the other end of the line in a horizontal direction, so that a measurement point that is closest to the sensor is extracted in each session of the step and the function describing a straight line approximating the curve through all of the thus extracted measurement points is determined by the least-squares method in order to determine the angle of the thus determined straight line with respect to a horizontal plane.

According to another aspect of the present invention, an apparatus for measuring the inclination angle of a pile of a powdery or granular material is provided with: a horizontal surface on which the powdery or granular material is stacked in a pile; a sensor, placed above the powdery or granular material stacked in a conical pile on the horizontal surface, that emits sensor light in a vertical direction toward a free surface of the pile of the powdery or granular material and, by receiving the light reflected from a spot illuminated by the sensor light, detects the distance to that spot; a moving means for moving the sensor in a horizontal direction within a vertical plane including the vertex of the pile of the powdery or granular material; and a control means for controlling the moving means and for processing the data obtained from the sensor. In this apparatus, the sensor is moved in a horizontal direction to detect the distance to each of a plurality of measurement points along a ridge line of the pile of the powdery or granular material, with the measurement points arranged along the ridge line at regular intervals in a horizontal direction, so that the function describing a straight line approximating the curve through those measurement points is determined by the least-squares method in order to determine the angle of the thus determined straight line with respect to a horizontal plane.

According to another aspect of the present invention, an apparatus for measuring the inclination angle of a pile of a powdery or granular material is provided with: a spatula supported horizontally; a sensor, placed by the side of a pile of the powdery or granular material stacked on the spatula, that emits sensor light in a horizontal direction toward a free surface of the pile of the powdery or granular material and, by receiving the light reflected from a spot illuminated by the sensor light, detects the distance to that spot; a moving means for moving the sensor in a vertical direction; and a control means for controlling the moving means and for processing the data obtained from the sensor. In this apparatus, the sensor is moved in a vertical direction to detect the distance to each of a plurality of measurement points along a line that runs on the free surface so as to face the movement path of the sensor, with the measurement points being arranged along the line at regular intervals in a vertical direction, so that the function describing a straight line approximating the curve through those measurement points is determined by the least-squares method in order to determine the angle of the thus determined straight line with respect to a horizontal plane.

According to another aspect of the present invention, a method of measuring the inclination angle of a pile of a powdery or granular material includes: a first step of placing a sensor that emits sensor light toward the powdery or granular material stacked in a conical pile on a horizontal surface and, by receiving the light reflected from a spot illuminated by the sensor light, detects the distance to the pile of the powdery or granular material in a measurement start position in which the sensor light illuminates an arbitrary spot on the pile of the powdery or granular material from a first direction that is not vertical; a second step of, within at least one plane that exists between the arbitrary spot and the vertex of the pile of the powdery or granular material and that is parallel to the first direction and parallel to a second direction perpendicular to the first direction, moving the sensor light in the second direction while measuring the distance from the sensor to the pile of the powdery or granular material in order to find a point on the pile of the powdery or granular material at which the distance is smallest; a third step of, within a vertical plane that includes a point selected from the thus found smallest-distance points and that is parallel to the first direction, moving the sensor light in a direction perpendicular to the first direction to detect a plurality of measurement points on the pile of the powdery or granular material; and a fourth step of determining the angle, with respect to a horizontal plane, of the straight line obtained by approximation from the positions of the plurality of measurement points.

According to another aspect of the present invention, an apparatus for measuring the inclination angle of a pile of a powdery or granular material is provided with: a table having a horizontal surface; a sensor, placed by the side of the powdery or granular material stacked in a conical pile on the horizontal surface of the table, that emits sensor light in a substantially horizontal first direction toward the pile of the powdery or granular material and, by receiving the light reflected from a spot illuminated by the sensor light, detects the distance to the pile of the powdery or granular material; a moving means for moving the sensor in a second direction that is horizontal and perpendicular to the first direction and in a third direction that is perpendicular to the first direction within a vertical plane including the optical axis of the sensor light; and a control means for controlling the moving means and for processing the data obtained form the sensor. In this apparatus, after the sensor is placed in a measurement start position in which the sensor light illuminates a point on the pile of the powdery and granular material, a first step in which the sensor is moved in the second direction a predetermined distance at a time within a substantially horizontal plane and, every time the sensor is so moved, the position of a point on the pile of the powdery or granular material that is illuminated by the sensor light is detected to find the point on the pile of the powdery or granular material at which the distance from the sensor to the pile of the powdery or granular material within the substantially horizontal plane is smallest, a second step in which the first step is performed every time the sensor is moved in the third direction a predetermined distance at a time, a third step in which the position in the second direction of the sensor is made to coincide with the position in the second direction of a point selected from the smallest-distance points found in the second step as points at which the distance from the sensor to the pile of the powdery or granular material within the substantially horizontal plane is smallest and, every time the sensor is moved in the third direction a predetermined distance at a time, the position of the measurement point on the pile of the powdery or granular material that is illuminated by the sensor light is detected, and a fourth step in which a straight line is determined by approximation from the data of the positions of a plurality of measurement points detected in the third step in order to determine the angle of the straight line with respect to a horizontal plane are performed.

According to another aspect of the present invention, an apparatus for measuring the inclination angle of a pile of a powdery or granular material is provided with: a spatula having a sample stage with a rectangular upper surface; a vat, placed below the spatula, on which the powdery or granular material is stacked in a pile; a first moving means for moving the vat vertically; a sensor that emits sensor light in a first direction perpendicular to the direction of the length of the spatula and, by receiving the light reflected from a spot illuminated by the sensor light on the pile of the powdery or granular material stacked on the sample stage, detects the distance to the pile of the powdery or granular material; a second moving means for moving the sensor in the direction of the length of the spatula and in a second direction perpendicular both to the direction of the length of the spatula and to the first direction; a shocker having a base joined to the spatula, an electromagnet placed above the base integrally therewith, and a weight placed so as to be vertically movable between the base and the electromagnet and made at least partially of a magnetic material, the weight being attracted to the electromagnet when the electromagnet is fed with an electric current, the weight dropping onto the base to deliver a shock to the spatula when the electric current to the electromagnet is cut off; and a control means for controlling the first and second moving means and the shocker and for processing the data obtained from the sensor. In this apparatus, the control means automatically controls and performs in predetermined order a predetermined number of times a first step in which the vat placed near the spatula and stacked with the pile of the powdery or granular material is moved downward, a second step of, every time the sensor is moved to a predetermined position, detecting the position of the point on the pile of the powdery or granular material that is illuminated by the sensor light, a third step of delivering a shock to the spatula by means of the shocker, and a fourth step of determining the spatula angle of the pile of the powdery or granular material from the data of a plurality of positions obtained in the second step.

BRIEF DESCRIPTION OF THE DRAWINGS

This and other objects and features of the present invention will become clear from the following description, taken in conjunction with the preferred embodiments with reference to the accompanied drawings in which.

DESCRIPTION OF THE PREFERRED EMBODIMENTS

Hereinafter, embodiments of the present invention will be described with reference to the drawings.

Figure 1:
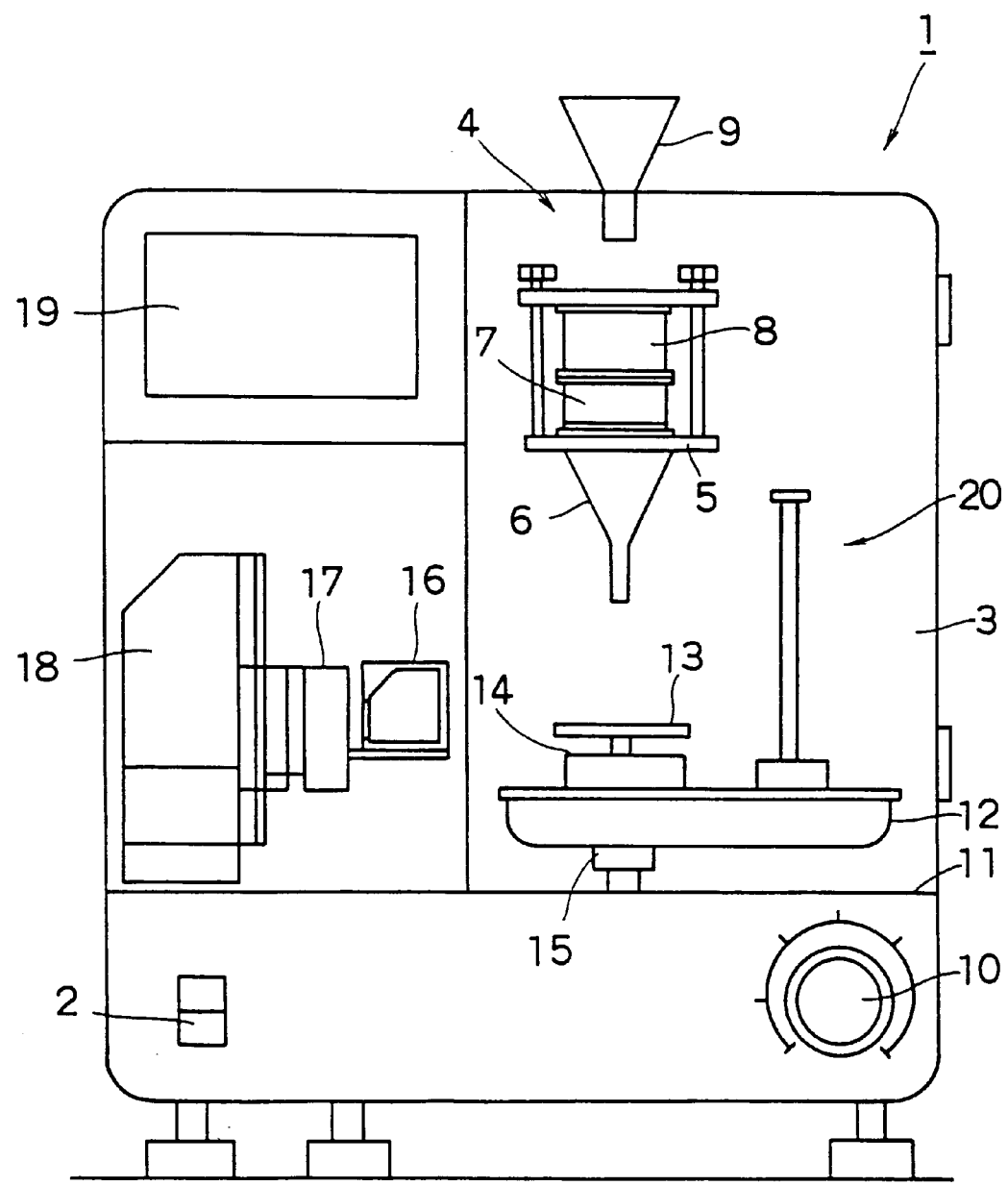
FIG. 1 is a front view of the measurement apparatus of a first embodiment of the invention.

FIG. 1 shows a measurement apparatus 1 that can measure seven properties that are considered to be the principal factors that determine the flow and jet characteristics of a powdery and granular material: angle of repose, condensation, spatula angle, cohesion, angle of collapse, dispersion, and difference angle. The apparatus 1 has, in its lower left-hand portion, a power switch 2 for turning the power on and off. The apparatus 1 has, in its right-hand portion, a measurement section, at the front of which is provided a transparent lid 3 made of a synthetic resin.

Above the measurement section is provided a vibration unit 4 for sifting the powdery or granular material by vibration to measure the angle of repose. The vibration unit 4 is mounted on a vibration base, and is provided with a measurement funnel 6, a sieve 7 placed above it, and a sieve presser 8 placed further above. Above the vibration unit 4 is placed a sample feed funnel 9 for feeding a sample powdery or granular material. The sieve presser 8 is used to temporarily store the powdery or granular material fed from the sample feed funnel 9. The sieve presser 8 has the same shape as the sieve 7 but does not have meshes. The vibration base 5 extends in a direction perpendicular to the plane on which FIG. 1 is drawn, and is supported at one end by the body of the apparatus 1. To the bottom surface of the vibration base 5, an absorber (not shown) is attached that is joined to an electromagnet (not shown) that is attached to the body of the apparatus 1 with a cushioning material in between, so that, by turning on and off the supply of an electric current to the electromagnet, the vibration base 5 vibrates vertically. The apparatus 1 has an amplification adjustment knob 10 for adjusting the amplitude of the vibration of the vibration base 5.

The bottom surface of the measurement section is formed into a measurement base 11, on which a seat (not shown) is provided to place a rectangular vat 12 on. Inside the rectangular vat 12 are placed, as shown in FIG. 1, a circular angle-of-repose measurement table 13, a volumetric-specific-gravity measurement unit (not shown), a cylindrical guide 14 for guiding an apparent-specific-gravity (looseness/tightness) measurement cup (not shown), a shocker 20 (described later, see FIG. 4), and others. The angle-of-repose measurement table 13 has a horizontal top surface. For the measurement of the spatula angle, a spatula-angle measurement unit 21 (described later, see FIG. 5) is placed instead of the angle-of-repose measurement table 13 and the guide 14. The above-mentioned measurement cup is moved vertically by a lift bar 15.

To the left of the portion in which the angle-of-repose measurement table 13 or the spatula-angle measurement unit 21 is placed, a sensor 16 is placed. The sensor 16 is attached to a movable block 17, which is moved by an actuator 18 in a horizontal direction (hereafter referred to as the X direction) perpendicular to the plane on which FIG. 1 is drawn and in a vertical direction (hereafter referred to as the Z direction).

Figure 2:
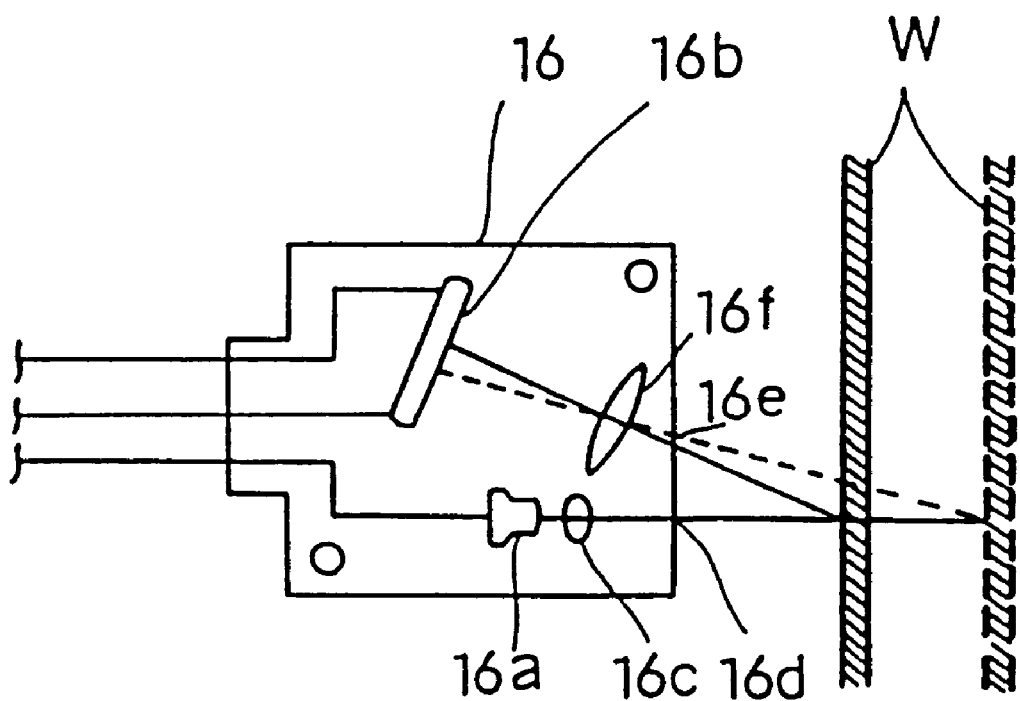
FIG. 2 is a diagram illustrating the structure of the sensor and the principle of the measurement.

As shown in FIG. 2, the sensor 16 is composed of a light-emitting device 16a and a light-sensing device 16b. As the light-emitting device 16a, a light-emitting diode or a semiconductor laser device is used. The light from the light-emitting device 16a is condensed by a condenser lens 16c, is then emitted through a light-emission opening 16d in a horizontal direction (rightward in FIG. 1) as sensor light, and is then shone onto a target object W to form a light spot on it. Part of the light diffused and reflected by the target object W enters the sensor 16 through a light-reception opening 16e, and is then shone through a light-reception lens 16f onto the light-sensing device 16b to form a light spot on it. This enables the sensor 16 to detect the distance to the spot on the target object W that is illuminated by the sensor light. The direction of the optical axis of the sensor light will hereafter be referred to as the Y direction.

Figure 3A:
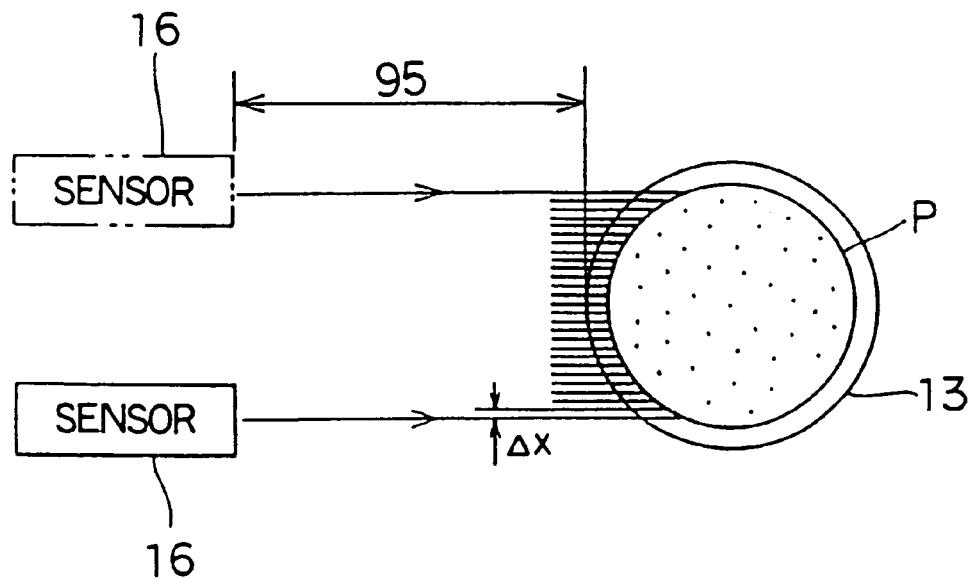
FIGS. 3A and 3B are diagrams illustrating how the measurement apparatus of FIG. 1 performs the measurement.
Figure 3B:
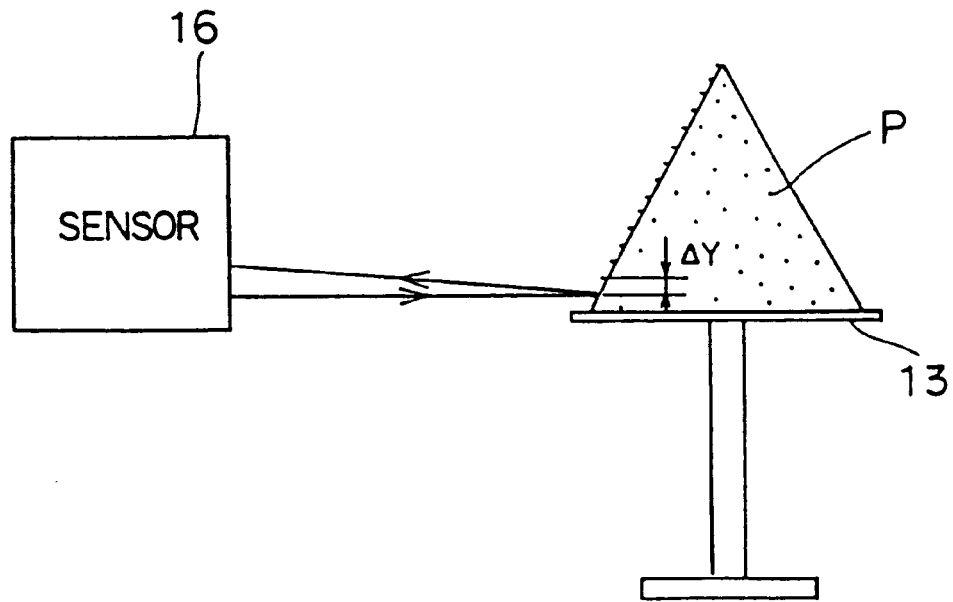

The sensor 16 used in this embodiment is a laser displacement sensor of the model Z4M-W100RA manufactured by OMRON Corporation, Japan. This sensor offers a measurement range of 100±40 mm, meaning that it cannot detect a point outside this range. As shown in FIG. 3A, the sensor 16 is placed 95 mm away from the facing edge of the table 13, and the table 13 is 80 mm across. The other measurement members and other components that are arranged around the table 13 are placed outside the measurement range of the sensor 16, so that the sensor 16 detects nothing other than the pile P of the powdery or granular material stacked on the table 13, and thus accurate measurement results can be obtained. It is of course possible to use a sensor of a different type from the one mentioned above.

As shown in FIG. 1, the measurement apparatus 1 has, in its upper left-hand portion, a computer 19 for controlling the measurement section, the sensor 16, the actuator 18, and other components. The computer 19 has operation keys provided on a touch panel, and a display unit composed of an LCD panel.

Figure 4:
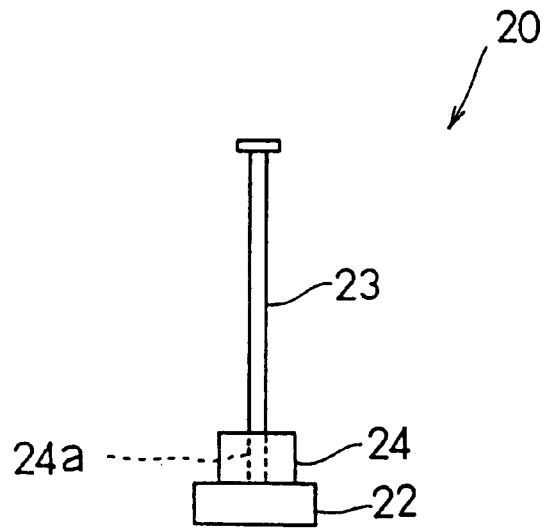
FIG. 4 is a side view of the shocker used in the measurement apparatus of FIG. 1.

FIG. 4 shows the shocker 20, which is used to measure the angle of collapse. The shocker 20 has a pole 23 mounted vertically on the top surface of a base 22, and a circular weight 24 having a through hole 24a at its center so as to be placed on the base 22 with the pole 23 put through the through hole 24. By lifting the weight 24 up to the top end of the pole 23 by hand and then letting it go, the weight 24 falls freely and delivers a shock to the base 22.

Figure 5:
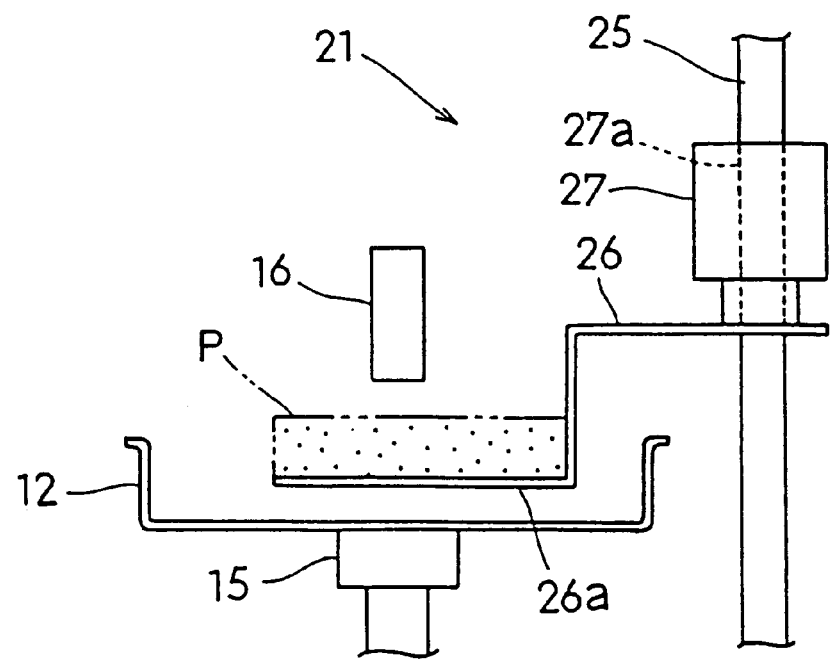
FIG. 5 is a side view of the spatula angle measurement unit used in the measurement apparatus of FIG. 1.

FIG. 5 shows the spatula-angle measurement unit 21, which has a pole 25 mounted vertically on a base (not shown), a spatula 26 extending in a lateral direction in FIG. 5 and attached at one end to the pole 25, and a circular weight 27 having a through hole 27a at its center and placed above the spatula 26 with the pole 25 put through the through hole 27a. By lifting the weight 27 up to the top end of the pole 25 and then letting it go, the weight 27 falls freely and delivers a shock to the spatula 26. The spatula-angle measurement unit 21 is placed in such a way that the sample stage 26a, which is formed in the free-end portion of the spatula 26 to stack the powdery or granular material P on, is situated inside the rectangular vat 12.

Having the structure as described above, the measurement apparatus 1 operates as follows.

First, how the angle of repose is measured will be described.

First, the measurement apparatus 1 is brought into a mode for angle-of-repose measurement by the operation of the operation keys provided in the computer 19. Then, the lid 3 is opened, and the angle-of-repose measurement table 13 is placed in the rectangular vat 12, right below the measurement funnel 6. In a case where the angle of collapse is also measured subsequently, the shocker 20 is also placed in the rectangular vat 12, near the angle-of-repose measurement table 13. Then, a sample powdery or granular material is fed into the sample feed funnel 9 so that it is stacked on the sieve 7 of the vibration unit 4.

Then, the lid 3 is closed, and the vibration unit 5 is started to vibrate by the operation of the operation keys provided in the computer 19. This causes the powdery or granular material to fall through the meshes of the sieve 7 and start to be stacked on the top surface of the angle-of-repose measurement table 13. When a conical pile of the powdery or granular material is formed on the table 13, the vibration of the vibration unit 4 is stopped by the operation of the operation keys provided in the computer 19.

Next, when a request for starting angle-of-repose measurement is fed in from the operation keys of the computer 19, the actuator 18 moves the sensor 16 to a position facing a point at one end of the bottom edge of the free surface of the pile of the powdery or granular material stacked on the table 13, and then the actuator 18 moves the sensor 16 horizontally to a position facing a point at the other end of the bottom edge of the pile of the powdery or granular material. As the sensor 16 is moved, it emits a laser beam to successively detect the distance to each of a plurality of measurement points arranged horizontally along a line that runs on the free surface of the pile P of the powdery or granular material so as to face the movement path of the sensor 16. These measurement points are arranged along the above-mentioned line at regular intervals as minute as ΔX (see FIG. 3A), starting at one end and ending at the other end of the line. The measurement results are stored in a memory provided in the computer 19.

Next, the actuator 18 moves the sensor 16 vertically upward by a distance of ΔY, and then the actuator 18 moves the sensor 16 horizontally in the direction opposite to the above-noted direction. There, the sensor 16, just in the same manner as described above, detects the distance to each of a plurality of measurement points along a line that runs on the free surface of the pile P of the powdery or granular material so as to face the movement path of the sensor 16. This step in which the sensor 16 is moved horizontally to detect the positions of points on the free surface of the pile P of the powdery or granular material is repeated every time the sensor 16 is moved vertically a distance AY at a time; that is, this step is performed at different levels over the entire height of the pile P of the powdery or granular material.

Figure 6:
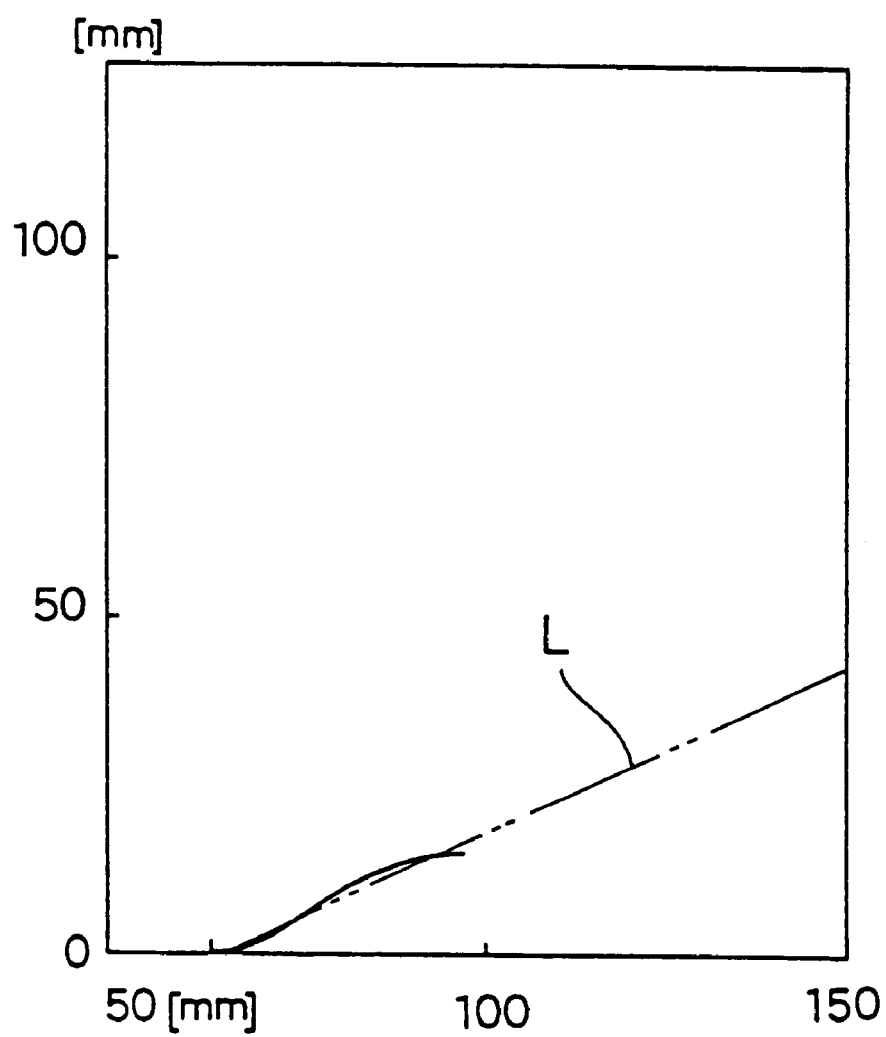
FIG. 6 is a graph showing the curve through the points found to be closest to the sensor and a straight line approximating that curve.

Next, the computer 19 extracts the point closest to the sensor 16 in each session of the above-mentioned step, and then determines, by the least-squares method, the function describing a straight line approximating the curve through all of the thus extracted points. Specifically, as shown in FIG. 6, when these points are plotted on a graph, with the distance to the sensor taken along the horizontal axis and the distance to the lowest among those points taken along the vertical axis, they describe a curve, as indicated by a solid line, that is almost straight. The computer 19 determines the function describing a straight line L that approximates this solid-lined curve by the least-squares method, determines the angle of this straight line L with respect to a horizontal plane, and displays the determined angle on the display unit as the inclination angle of the free surface of the pile P of the powdery or granular material.

When the angle of collapse is measured subsequently, the measurement apparatus is then brought into a mode for angle-of-collapse measurement by the operation of the operation keys of the computer 19. Then, the weight 24 of the shocker 20 is lifted up to the top end of the pole 23 and is released to drop onto the base 22 and thereby deliver a shock to the rectangular vat 12. This is repeated three times. This causes the pile P of the powdery or granular material stacked on the table 13 to collapse, with the result that the free surface of the pile now exhibits a smaller inclination angle. When a request for starting measurement is fed in from the operation keys, the inclination angle of the free surface of the pile P of the powdery or granular material is determined through the same procedure as for angle-of-repose measurement, and the determined angle is displayed on the display unit as the angle of collapse.

When the difference angle is measured subsequently, the measurement apparatus is brought into a mode for difference-angle measurement. Then, the difference between the angle of repose and the angle of collapse stored in the memory is determined, and is displayed on the display unit as the difference angle.

Figure 7:
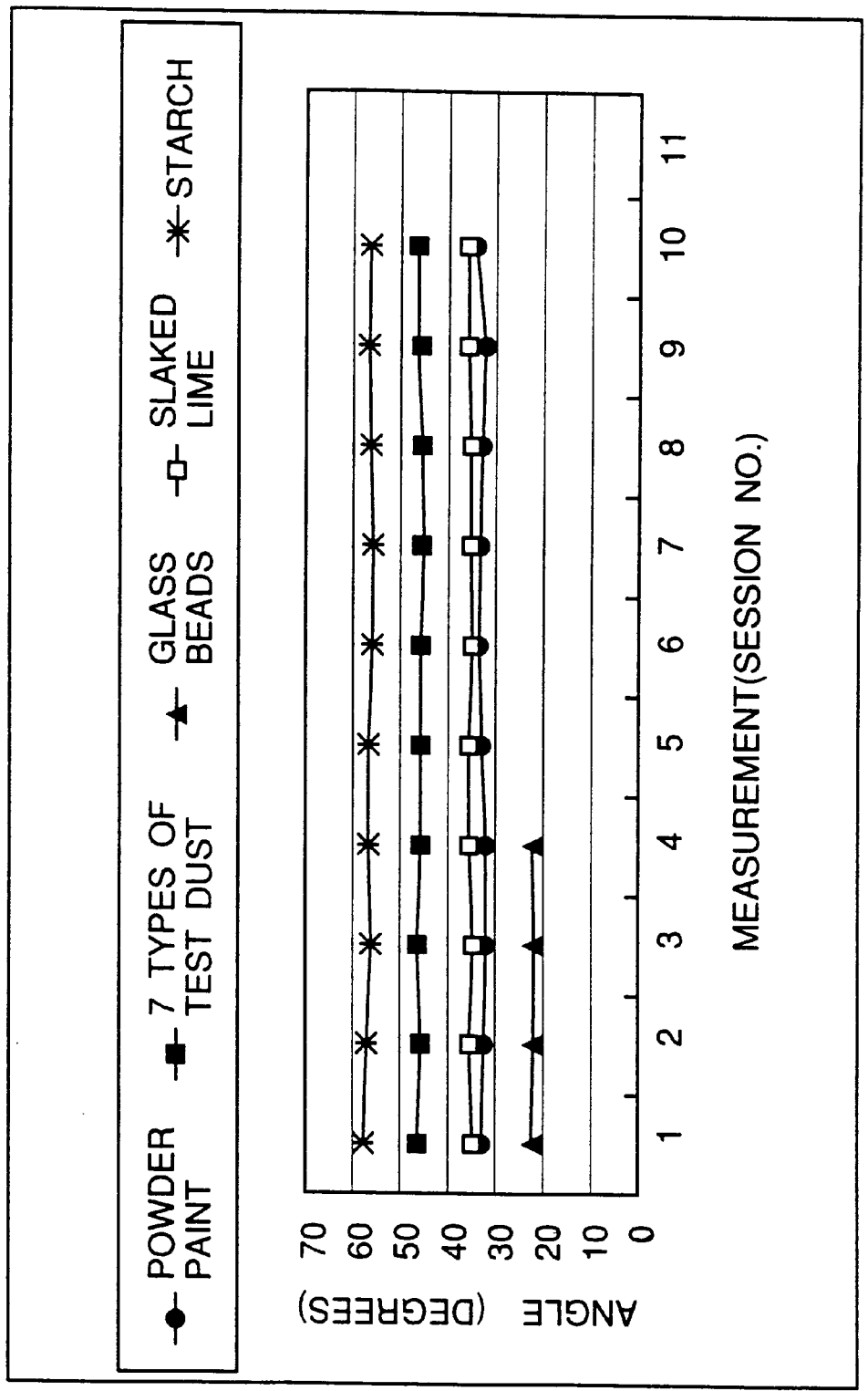
FIG. 7 is a graph showing the results of measurement of the angle of repose of various powdery or granular materials.

FIG. 7 is a graph showing the results of measurement of the inclination angle (angle of repose) conducted several times with the state of the pile intact for each of various powdery or granular materials. As this graph shows, it is possible to obtain almost constant measurement results substantially free from variations.

According to the present invention, instead of putting a protractor on the free surface of a powdery or granular material as practiced conventionally, the inclination angle is determined by the least-squares method, which is a well-established method. As a result, the measurement results are not affected by how a measurer conducts the measurement, but are always consistent regardless of who conducts the measurement. In addition, the method according to the present invention does not involve difficult manipulation of a protractor as noted above, and thus requires less effort and time to conduct the measurement (e.g. to conduct a session of measurement, it takes about 10 seconds, as compared with about 20 to 30 seconds required by the conventional method).

Next, how the spatula angle is measured will be described.

First, the measurement apparatus is brought into a mode for spatula-angle measurement by the operation of the operation keys of the computer 19. Then, the lid 3 is opened, and, as shown in FIG. 5, the spatula-angle measurement unit 21 is placed between the rectangular vat 12 and the rear wall of the measurement section. Then, by the use of the lift bar 15, the rectangular vat 12 is lifted to a position in which its base surface comes into contact with the bottom surface of the sample stage 26a of the spatula 26. Then, by the use of a spoon for example, a sample powdery or granular material P is stacked on the sample stage 26a to form a pile thereon, and the rectangular vat 12 is moved downward by the use of the lift bar 15.

When a request for starting measurement is fed in from the operation keys, the actuator 18 moves the sensor 16 to a position obliquely above the sample stage 26a of the spatula 26, and then the actuator 18 moves the sensor 16 vertically downward. As the sensor 16 is moved, it emits a laser beam to successively detect the distance to each of a plurality of measurement points arranged vertically along a line that runs on the free surface of the powdery or granular material P so as to face the movement path of the sensor 16. These measurement points are arranged along the above-mentioned line at regular intervals. The detected distances are stored in the memory of the computer 19. The computer 19 then determines, through the same procedure as described previously, the function describing a line approximating the curve through these points, determines the angle of this line with respect to a horizontal plane, and stores it in the memory.

Next, the computer 19 moves the sensor 16 in the direction of the length of the spatula 26 by a predetermined distance, then moves the sensor 16 vertically upward, then determines the inclination angle of the free surface of the pile P of the powdery or granular material through the same procedure as described previously, and then stores the determined angle in the memory. Thereafter, the computer 19 moves the sensor 16 in the direction of the length of the spatula 26 by a predetermined distance, then moves the sensor 16 vertically downward, and then determines the inclination angle of the free surface of the pile P of the powdery or granular material.

The computer 19 then calculates the average of a plurality of inclination angles thus obtained, and displays the calculated value on the display unit as the spatula angle before collapse. The measurer stores this angle in memory by the operation of the operation keys. Note that the inclination angle may be measured only in one position, but that calculating the average value of a plurality of inclination angles measured in different positions as described above contributes to higher measurement accuracy.

Next, the measurer lifts the weight 27 up to the top end of the pole 25 and then lets it fall to deliver a shock to the spatula 26 (only once). This causes the pile P of the powdery or granular material stacked on the spatula 26 to collapse, and then its free surface exhibits a smaller inclination angle. When a request for starting measurement is fed in from the operation keys, the inclination angle is measured in three different positions on the pile P of the powdery or granular material through the same procedure as described previously, and the measured angle is displayed on the display unit as the spatula angle after collapse.

When this inclination angle is stored by the operation of the operation keys, the average of the spatula angles before and after collapse is calculated and displayed on the display unit.

Figure 8:
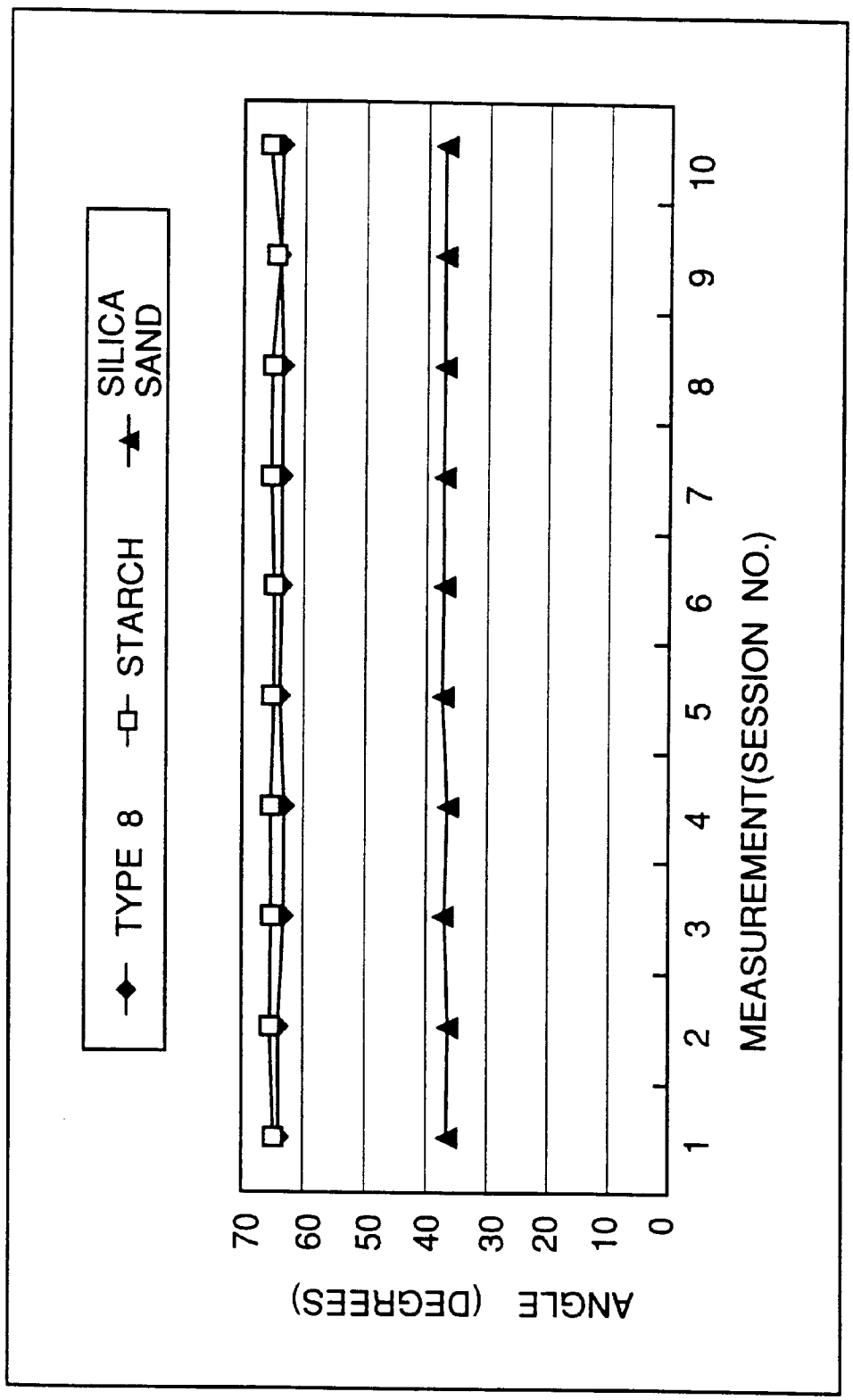
FIG. 8 is a graph showing the results of measurement of the spatula angle of various powdery or granular materials.

FIG. 8 is a graph showing the results of measurement of the spatula angle conducted several times with the state of the pile intact for each of various powdery or granular materials. Note that "Type 8" denotes a standard sample as defined in JIS (Japanese Industrial Standard) which is made chiefly of a powdery or granular material obtained from the loam layer of the Kanto district of Japan. As this graph shows, it is possible to obtain almost constant measurement results substantially free from variations.

This measurement apparatus 1 adopts well-known structures for the measurement of the properties other than the angle of repose and the spatula angle, and therefore no explanation will given as to the design and use of those structures.

Next, a second embodiment of the present invention will be described.

Figure 9:
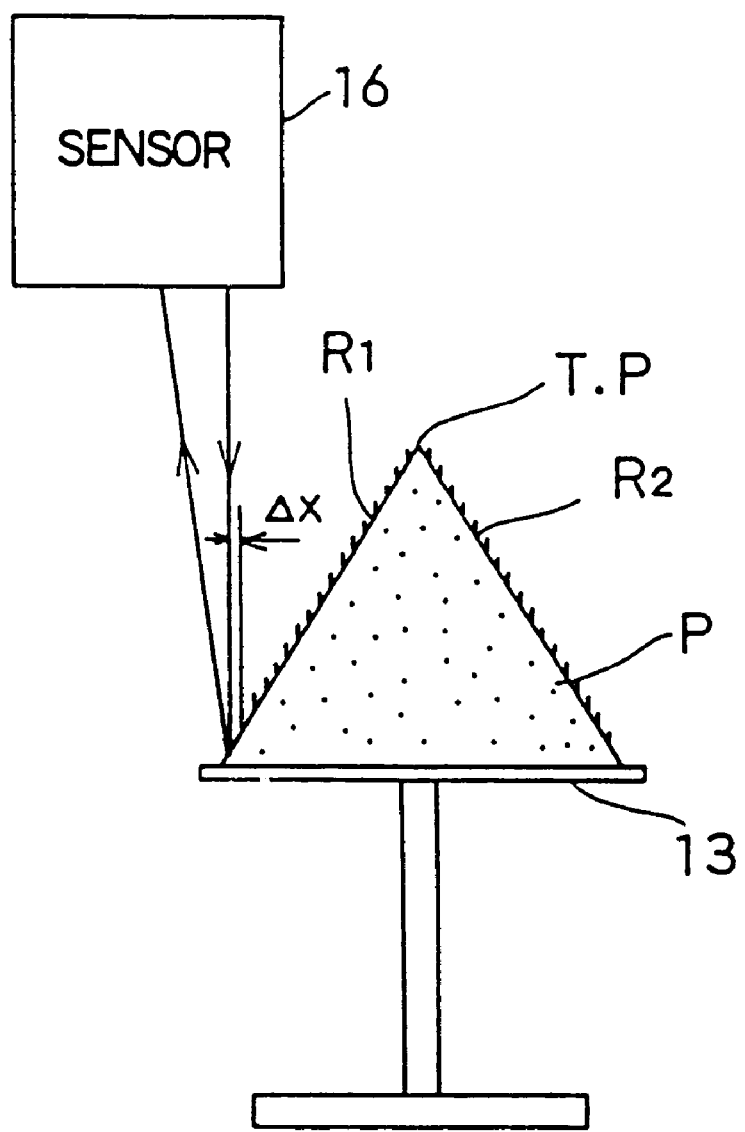
FIG. 9 is a diagram illustrating the measurement method used in a second embodiment of the invention.

As shown in FIG. 9, in this embodiment, the sensor 16 is placed above the pile P of a powdery or granular material stacked on the angle-of-repose measurement table 13, so that the sensor 16 emits sensor light vertically downward to detect the distance to the illuminated spot on the free surface of the pile P of the powdery or granular material. The computer 19 moves the sensor 16 horizontally within a vertical plane including the vertex T.P of the pile P of the powdery or granular material, measures the distance to each of a plurality of measurement points arranged horizontally at regular intervals ΔX along a ridge line R1 on one side of the vertex T.P of the pile P of the powdery or granular material, determines the function of a straight line approximating the curve through these points through the same procedure as described previously, determines the angle of this straight line with respect to a horizontal plane, and stores the obtained angle in the memory as the inclination angle of the free surface of the pile P of the powdery or granular material. The same sequence of operations is performed also on the opposite side of the vertex T.P to determine the angle, with respect to a horizontal plane, of a line approximating the curve through a plurality of measurement points along the ridge line R2 and store the obtained angle in the memory. Then, the computer 19 calculates the average of the two inclination angles obtained, and displays it on the display unit as the inclination angle of the pile P of the powdery or granular material.

Note that the inclination angle may be measured only on one side of the vertex of the pile of the powdery or granular material, but that calculating the average of the inclination angles measured on both sides of the vertex as described above contributes to higher measurement accuracy.

Next, a third embodiment of the present invention will be described. Note that, in the following descriptions, no explanation will be given as to such components as are found also in the previously-described embodiments.

Figure 10:
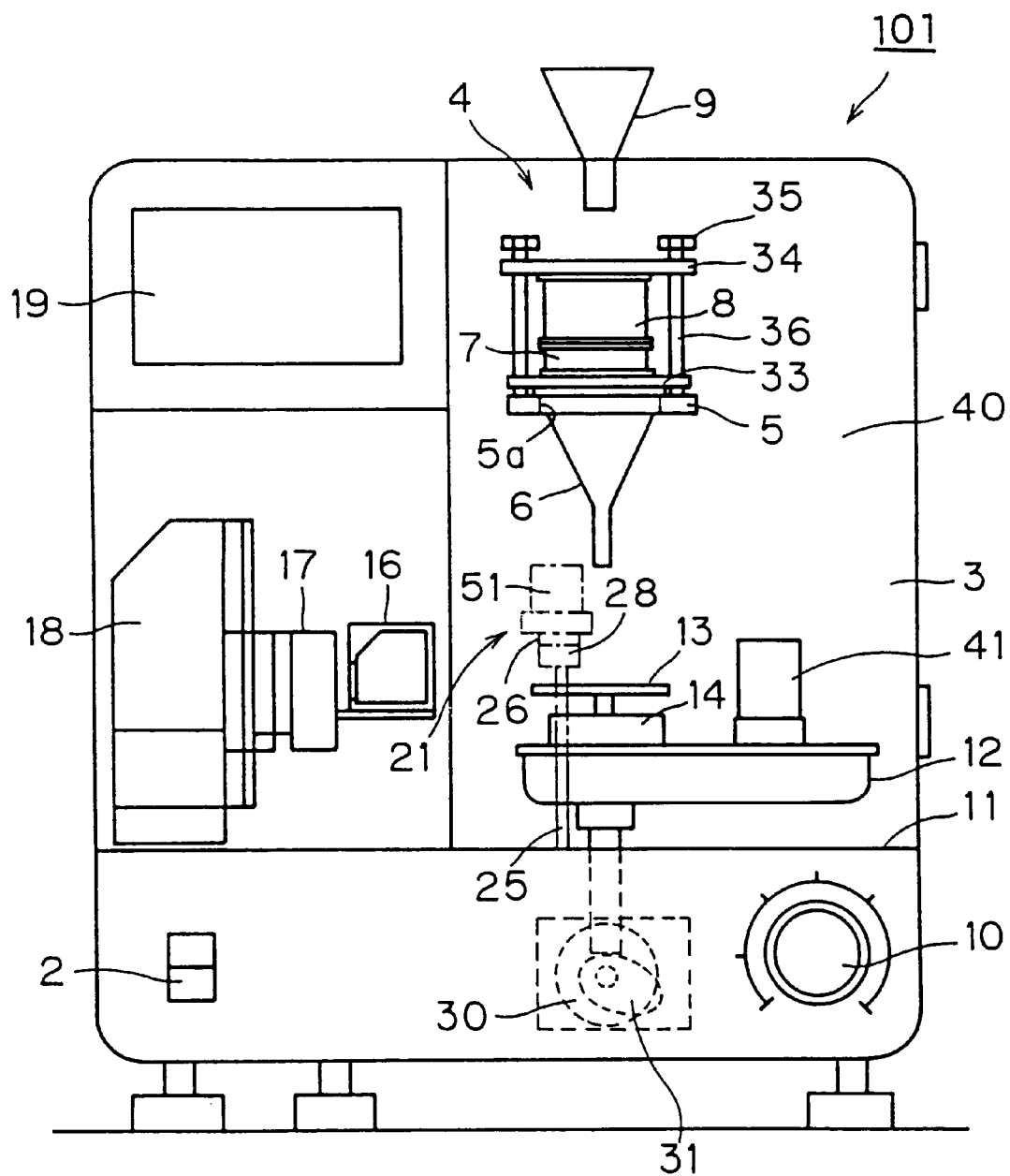
FIG. 10 is a front view of the measurement apparatus of a third embodiment of the invention.

In the measurement apparatus 101 of this embodiment, as shown in FIG. 10, the rectangular vat 12 is so supported that it is vertically movable by the action of a cam 31 connected to a lifting motor 30, and a shocker 41 is mounted on the rectangular vat 12. The guide 14 for supporting the angle-of-repose measurement table 13 is, when the apparent-specific-gravity (looseness/tightness) is measured, used to support a measurement cup (not shown) instead of the table 13. When the spatula angle is measured, the table 13, the guide 14, and the shocker 41 are removed, and instead the spatula-angle measurement unit 21 is mounted.

In the spatula-angle measurement unit 21, a spatula 26 is fixed to a pole 25 through a fixture 28, and a shocker 51 is fixed above the spatula 26. The shocker 51 has the same structure as the shocker 41, and therefore it is possible to design and use a single shocker for these two purposes.

In the vibration unit 4, the vibration base 5 has a through hole 5a, into which the measurement funnel 6 is inserted. The measurement funnel 6 and the sieve 7 are positioned on the vibration base 5 by the use of a space ring 33. The vibration base 5 has poles 36 mounted vertically thereon that have screw threads (not shown) formed in their top portions so that, by screw-engaging the poles 36 with nuts 35 and tightening them, the measurement funnel 6, the space ring 33, the sieve 7, and the sieve presser 8 are held between the vibration base 5 and a sieve presser bar 34.

Having the structure as described above, the measurement apparatus 101 is operated in the following manner to measure the angle of repose.

In FIG. 10, a powdery or granular material fed from the sample feed funnel 9 is made to pass through the meshes of the sieve 7 by the vibration of the vibration base 5. The grains then fall from the measurement funnel 6 onto one point on the table 13 and form thereon a conical pile of the powdery or granular material. By the operation of the operation keys of the computer 19, the sensor 16 is so positioned that its X-direction position substantially coincides with the X-direction position of the center of the table 13 and that its Z-direction position comes above the pile P of the powdery or granular material.

Figure 11A:
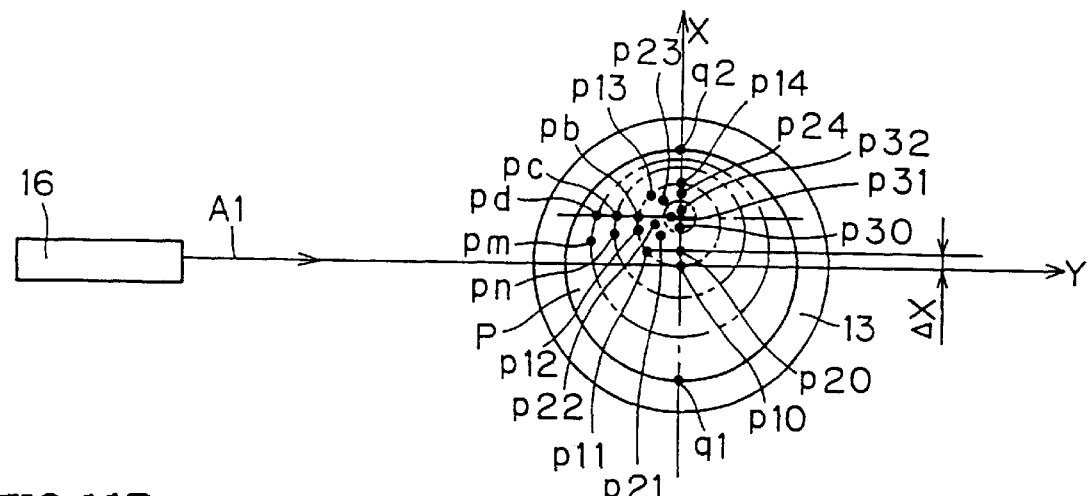
FIGS. 11A and 11B are diagrams illustrating how the measurement apparatus of FIG. 10 performs the measurement.

The movement of the sensor 16 will be described below with reference to FIGS. 11A and 11B. In FIG. 11A, dash-dot-dot lines represent contour lines. The measurement is performed taking into account also such cases where the X-direction position of the vertex q0 of the pile P of the powdery or granular material does not coincide with the center of the table 13, so that the same procedure of measurement is used regardless of whether they coincide or not.

The sensor 16, at first positioned such that the sensor light A1 does not strike the pile P of the powdery or granular material, is moved downward until it reaches a position and is stopped there (measurement start position) where the sensor light A1 starts illuminating the pile P of the powdery or granular material. In the figure, point p10 represents the point at which the sensor light A1 starts illuminating the pile P of the powdery or granular material. The computer 19 determines the position of point p10 on the basis of the distance data fed from the sensor 16 and the position data fed from the actuator 18. Next, every time the sensor 16 is moved in the X direction a predetermined distance ΔX at a time, the position of each of points p11 to p13 at which the pile P of the powdery or granular material is illuminated is detected, and the position data of the point (p12 in the case shown in FIG. 10) that is closest to the sensor 16 is stored.

Next, the sensor 16 is moved upward by a predetermined distance ΔZ, and then, in the same manner as described above, the position of each of points p20 to p24 is detected, and the position data of point p22, which is closest to the sensor 16, is stored. Then, similarly, the sensor 16 is moved upward by a predetermined distance ΔZ, the position of each of points p30 to p32 is detected, and the position data of point p31, which is closest to the sensor 16, is stored.

Next, in the same manner as described above, the sensor 16 is moved upward by a predetermined distance ΔZ, and the sensor 16, every time it is moved in the X direction a predetermined distance ΔX at a time, tries to detect a point at which the pile P of the powdery or granular material is illuminated. However, this time, as shown in FIG. 11B, the sensor light passes over the pile P of the powdery material, and thus the computer 19 recognizes that there is no object to be measured at that level and proceeds to the next sequence of operations. The upward movement of the sensor 16 may be repeated, as described above, until the pile P of the powdery or granular material ceases to be illuminated, or alternatively may be repeated a predetermined number of times.

Next, out of the points (p12, p22, and p31) of which each is found to be closest to the sensor 16 within one of the horizontal planes a predetermined distance ΔZ apart, one point (p31) is extracted, and the sensor 16 is moved to a position at the same X-direction position as that point and at a predetermined Z-direction position.

The extraction of one point is achieved, for example, by selecting the highest point; this is advantageous because, in a case as shown in FIG. 11A where the vertex of the conical pile P of the powdery or granular material is deviated, the higher the point, the smaller its X-direction deviation from the vertex. However, it is also possible to select the second highest point, in particular when the data obtained at the highest point is abnormal. Alternatively, it is also possible, in a case as shown in FIG. 12 where the ridge line of the vertical section of the pile P of the powdery or granular material describes a curve and the inclination angle is supposed to be measured within a predetermined range F, to select the point closest to (but not inside) the predetermined range F (i.e. p42 in FIG. 11). These extraction methods may be preprogrammed in the measurement apparatus, or alternatively they may be realized by appropriate operation of the measurement apparatus by the user.

Next, every time the sensor 16 is moved a predetermined distance ΔZ1 at a time, the positions of points pa to pd, on a single vertical plane, at which the pile P of the powdery or granular material is illuminated is detected, the function of a straight line approximating the curve through these points is calculated, and the angle (angle of repose) of the approximating straight line with respect to a horizontal plane is determined. Where necessary, it is also possible to detect the positions of points pa to pd more than once and calculate the average of the obtained angles of repose. This will contribute to higher measurement accuracy.

Figure 13A:
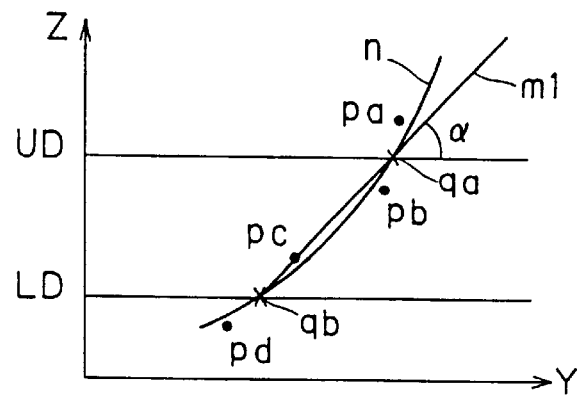
FIGS. 13A to 13C are diagrams illustrating how a straight line is approximated from the data obtained by the measurement.
Figure 13B:
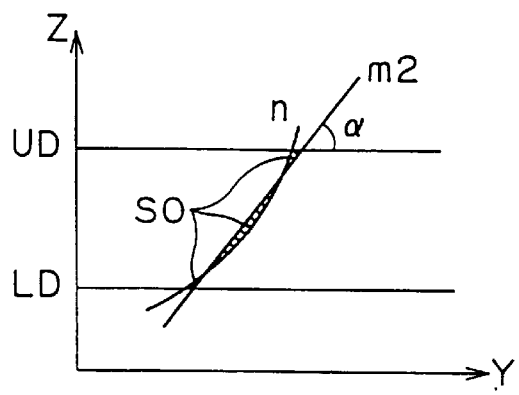

The determination of the function of the approximating straight line is achieved by determining a linear function by the least-squares method as in the previously described embodiments. Alternatively, it can also be achieved by, as shown in FIG. 13A, first determining the function of the curve n to be approximated that goes through points pa to pd by the least-squares method and then determining the line m1 through the intersections qa and qb at which the curve n intersects the upper and lower limits UD and LD of the predetermined range or, as shown in FIG. 13B, determining the line m2 that minimizes the area S0 enclosed by the curve n and the upper and lower limits UD and LD of the predetermined range. The approximating straight line may be determined by any other method. The predetermined range may be from the lowest to the highest point of the measurement range, or may be from the lowest to the highest point of the pile of the powdery or granular material.

Figure 13C:
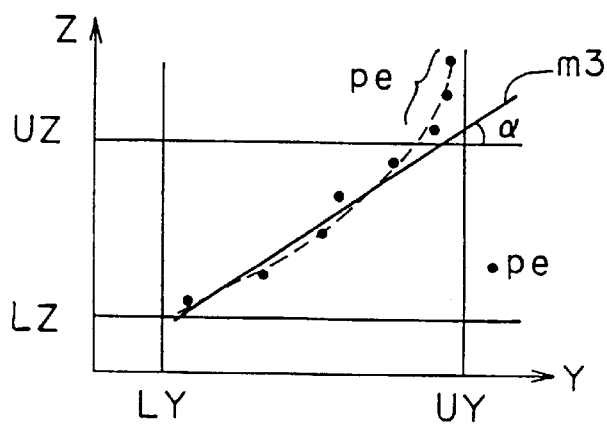

On the other hand, by making it possible to set the effective range of the measured data (from LZ to UZ, and from LY to UY), it is possible to determine an approximating straight line m3 excluding the data of measurement points, such as pe, outside the effective range. This helps ensure accurate calculation that is not affected by abnormal data or data outside the desired range. It is also possible to set the effective range in advance and thereby prevent the sensor mechanically from moving out of the effective range, or prevent data outside the effective range from being stored. Note that, in FIGS. 13A to 13C, the position in the Y direction is taken along the horizontal axis, and the position in the Z direction is taken along the vertical axis.

Figure 11B:
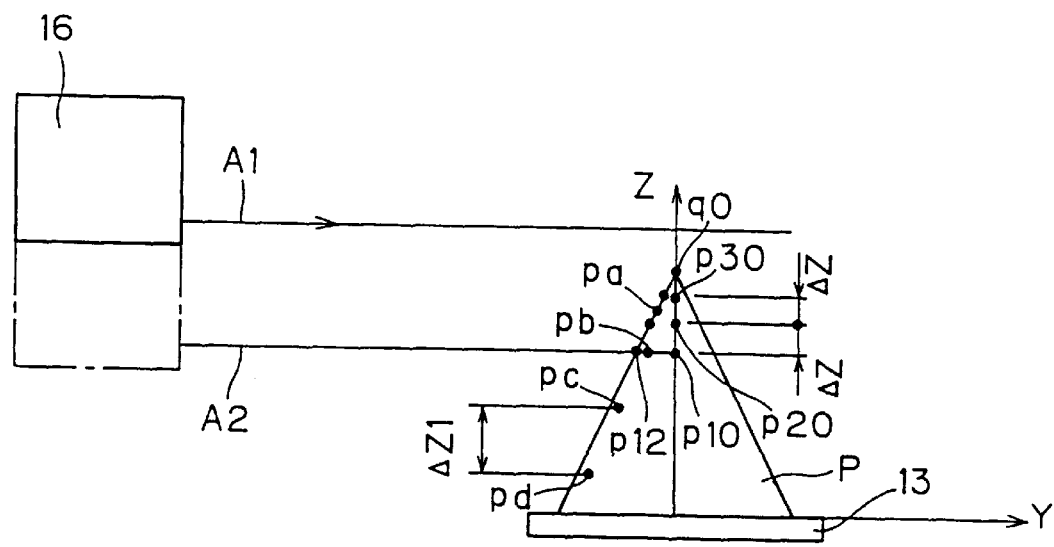
Figure 12:
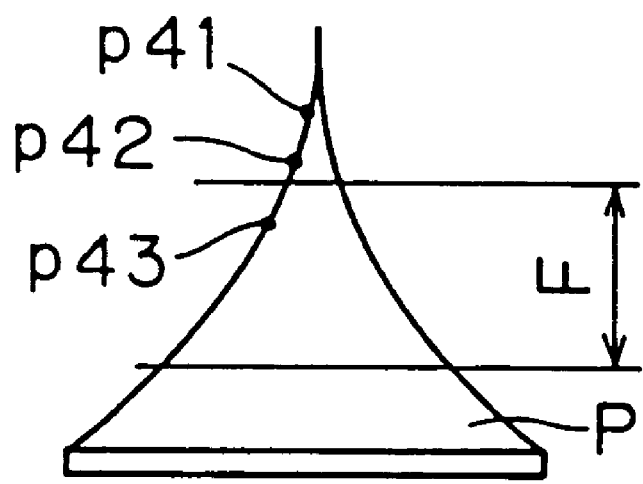
FIG. 12 is a side view illustrating how the measurement apparatus of FIG. 10 performs the measurement.

As shown in FIGS. 11A and 11B, the angle of repose thus determined takes the middle value between the inclination angle of the steeper slope from the vertex q0 of the pile P of the powdery or granular material to point q2 and the inclination angle of the gentler slope from the vertex q0 of the pile P of the powdery or granular material to point q1. This value is likely to take a different value every time the pile P of the powdery or granular material is formed. Accordingly, to achieve accurate measurement, it is necessary to form the pile P of the powdery or granular material more than once and measure the angle of repose each time in order to calculate the average.

According to the method used in the first embodiment, the approximating straight line is determined on the basis of the position data of points p12, p22, p31, pn, and pm, and the middle value between the inclination angle of the steeper slope and the inclination angle of the gentler slope is taken.

The first embodiment requires a sufficiently large data area for the storage of the data of the detected points so that the data of all the points on the lowest horizontal plane Q1 (see FIG. 11A), which presents the largest measurement range, can be stored. However, handling a large amount of data like this necessitates too much time being spent in moving the sensor 16 for position detection, transferring the obtained data to the computer 19, and performing other operations.

By contrast, in this embodiment, the measurement start point p10 is placed in the upper part of the pile P of the powdery or granular material, and therefore the points that are detected every time the sensor 16 is moved in the X direction a predetermined distance ΔX at a time are placed exclusively in the upper part of the pile P of the powdery or granular material. This helps reduce the number of measurement points and thereby reduce the time required for measurement, and in addition helps reduce the area required for data storage.

Moreover, in this embodiment, the sensor 16, at first positioned above the pile of the powdery or granular material, is first moved downward while it is emitting sensor light, and then the position of the sensor 16 in which it starts illuminating the pile P of the powdery or granular material is used as the measurement start point. This permits the sensor 16 to be positioned in the measurement start position automatically, and thus helps facilitate the measurement operation.

As described already, the sensor 16 is first moved downward from its initial position to detect the measurement start point p10. However, thereafter, the measurement apparatus cannot correctly judge whether to move the sensor 16 in the X positive or X negative direction. Accordingly, the sensor 16 is first moved in one direction and, if the pile P of the powdery or granular material is not detected in that direction, then the sensor 16 is moved in the opposite direction. This involves unnecessary movement of the sensor 16.

Figure 14:
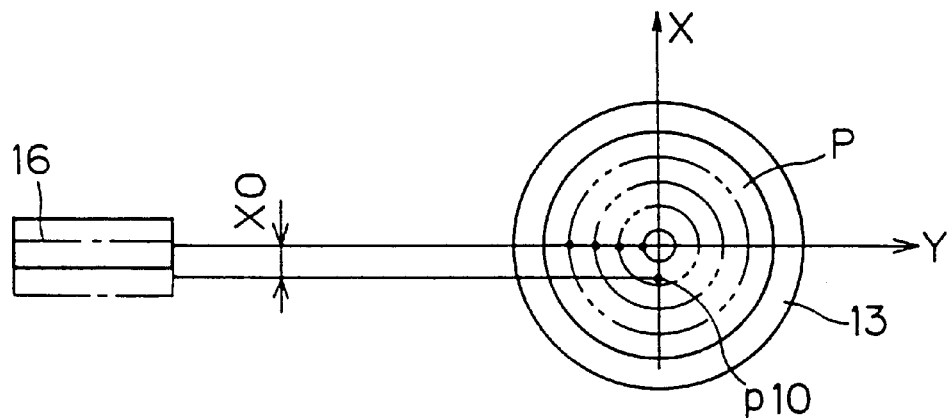
FIG. 14 is a diagram illustrating how the measurement apparatus of FIG. 10 performs the measurement.

To overcome this inconvenience, as shown in FIG. 14, the sensor 16 is first positioned a predetermined distance X0 away from the center of the table 13, is then moved downward to detect the measurement start point (p10), and is then moved in a predetermined direction of the X direction to perform measurement. This helps eliminate unnecessary movement of the sensor and thereby reduce the measurement time.

In this embodiment, the measurement start point (p10) is automatically detected. However, it is also possible to manually position the sensor 16 in a position in which the sensor light strikes a spot on the pile P of the powdery or granular material and use that position as the measurement start point.

In this embodiment, the sensor 16 emits sensor light in a horizontal direction. However, to achieve the detection of measurement points including the point closest to the sensor 16 as performed in this embodiment, the sensor light does not necessarily have to be emitted in a horizontal direction, but may be emitted in any direction as long as it is possible to detect a spot illuminated by the sensor light on the pile P of the powdery or granular material by moving the sensor 16 in a horizontal direction perpendicular to the optical axis of the sensor 16 and in a direction perpendicular to the optical axis of the sensor 16 within a vertical plane, and as long as the optical axis of the sensor 16 is not vertical.

Next, a description will be given as to how the measurement funnel 6 is supported in the vibration unit 4 (see FIG. 10) for forming a pile of the powdery or granular material.

Figure 15:
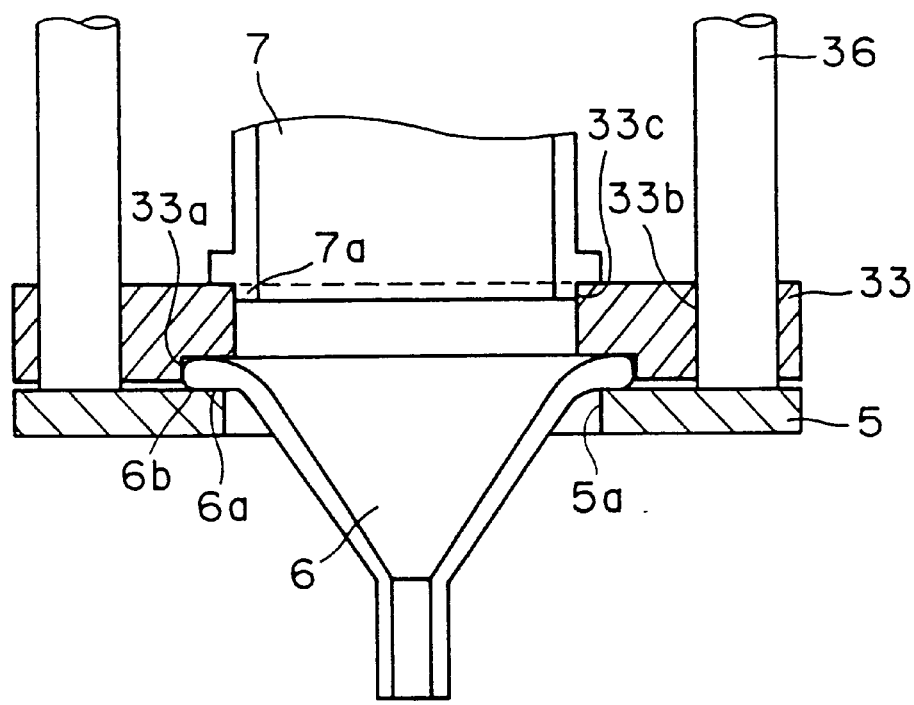
FIG. 15 is a vertical section of the vibration unit in the measurement apparatus of FIG. 10.

As shown in FIG. 15, the measurement funnel 6 is inserted into the though hole 5a of the vibration base 5, and its largest-diameter portion 6b is engaged with a counterbore 33a formed in the space ring 33. The space ring 33 is engaged with the poles 36 vertically mounted on the vibration base 5, and is thereby positioned horizontally. The space ring 33, together with the sieve 7 and other parts, is secured in position by being tightened from above with the nuts 35, with the sieve presser 34 (see FIG. 10) in between.

Figure 16A:
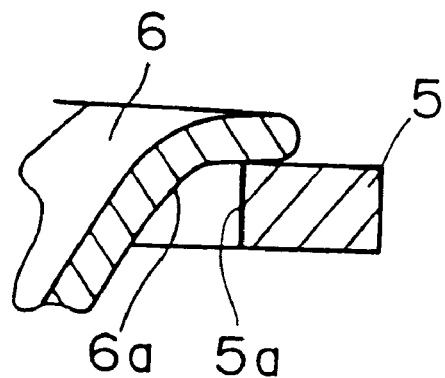
FIG. 16A is a vertical section showing how the funnel is supported in the measurement apparatus of FIG. 1.
Figure 16B:
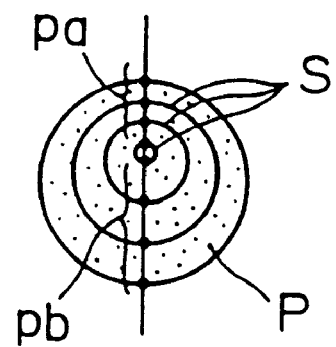
FIG. 16B is a diagram illustrating the problem that arises when the funnel is supported as shown in FIG. 16A.

In the first embodiment, as shown in FIG. 16A, the portion 6a of the measurement funnel 6 at which it engages with the through hole 5a of the vibration base 5 is formed in the lower-jaw-like portion of the measurement funnel 6 in which it has a diameter small than the through hole 5a. This often causes the measurement funnel 6 to be placed with its center deviated. In such a case, when the powdery or granular material is dropped onto the table 13 to form a pile P thereon, the pile P takes, as shown in FIG. 16B, a conical shape having a deviated vertex and having contour lines as indicated by S. As a result, different inclination angles between the maximum inclination obtained from the points pa and the minimum inclination obtained from the points pb can be obtained depending on the position of the vertex. This causes variations in the measured values.

In this embodiment, which has the structure as described previously, the measurement funnel 6 is accurately positioned both vertically and horizontally on the vibration base 5 by the space ring 33. This makes it possible to form a pile P of the powdery or granular material with a minimum distance from the center of its base to its vertex as projected on the base, and thus to obtain an accurately conical pile. This helps increase measurement accuracy and eliminate variations in results of repeated measurement.

Next, a description will be given as to the shocker 41 used to deliver a shock to the pile P of the powdery or granular material during the measurement of the angle of collapse.

With the shocker 20 (see FIG. 4) of the first embodiment, the user manually operates the weight, and therefore the gap between the pole 23 and the through hole 24a of the weight 24 allows the weight 24 to tilt. Moreover, although the user is expected to let the weight fall freely, the user may unconsciously push the weight downward. Thus, it is difficult to make the weight 24 collide with the base 22 in a fixed manner to obtain a stable shock, and therefore variations in measurement results are inevitable.

Figure 17:
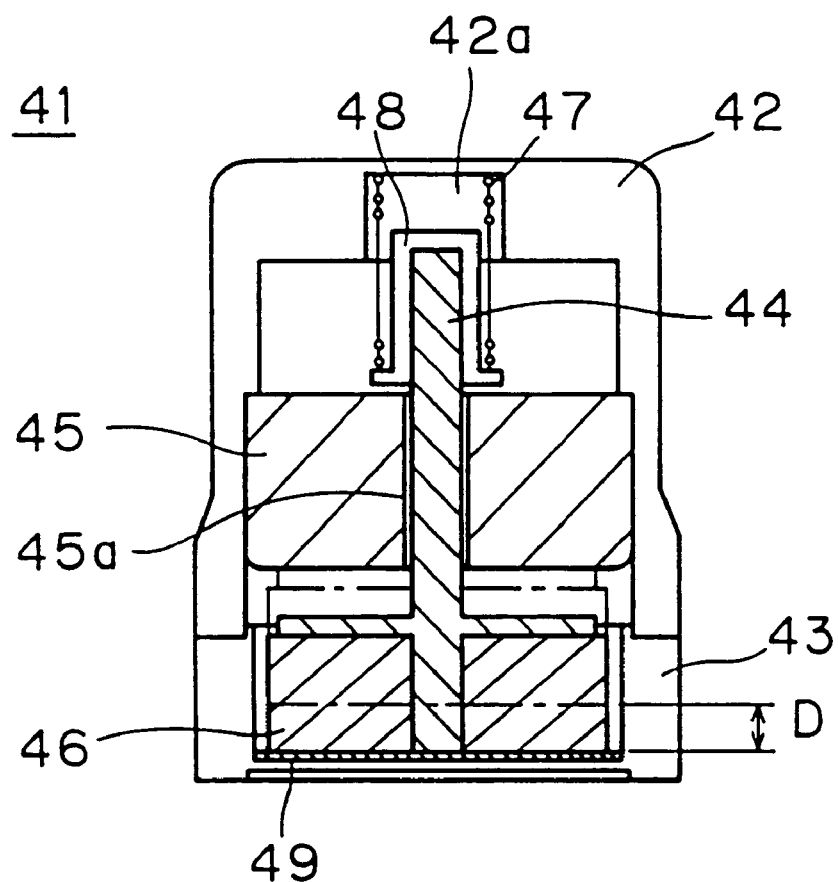
FIG. 17 is a vertical section of the shocker used in the measurement apparatus of FIG. 10.

As shown in FIG. 17, in this embodiment, the shocker 41 has an electromagnet 45 fixed to a top cover 42, and the electromagnet 45 has a through hole 45a, through which a movable shaft 44 is fitted so as to be vertically movable. The bottom end of the movable shaft 44 is fixed to the weight 46. The top cover 42 has a hole 42a formed in its top portion, and a compressed spring 47 is inserted into this hole 42a so that the compressed spring 47 presses downward a cap 48, into which the movable shaft 44 is fitted. The movement stroke D of the movable shaft 44 and the weight 46 is limited by the bottom surface of the electromagnet 45 and the base surface of a bottom cover 43. The bottom cover 43 is fixed to the top cover 43, and its base surface is lined with a cushioning material 49 such as rubber.

Having the structure as described above and placed above the rectangular vat 12 (see FIG. 10), the shocker 41 operates as follows. When the electromagnet 45 is fed with an electric current, the weight 46 is attracted upward, and, when the supply of the electric current is cut off, the weight 46 falls onto the cushioning material 49 and thereby delivers a shock to the table 13 that is connected to the rectangular vat 12, causing the pile P of the powdery or granular material to collapse. Compared with the conventional method in which the weight is lifted by hand and then released to fall and thereby deliver a shock, this method, in which such operations are controlled electrically, allows operation from outside the measurement apparatus 101 and thus offers a higher degree of user-friendliness; it also makes it possible to deliver a stable shock. Thus, this method helps reduce variations in results of repeated angle-of-collapse measurement.

The compressed spring 47 is provided to detach the movable shaft 44 and the weight 46 from the electromagnet 45 immediately after the electric current to the electromagnet 45 is cut off. This helps prevent, after the cutting-off of the electric current to the electromagnet 45, the movable shaft 44 and the weight 46 from being attracted to the electromagnet 45 for a while. The cushioning material 49 prevents irregular shocks from being delivered to the pile P of the powdery or granular material by the bounding movement of the dropped weight.

Next, how the spatula angle is measured will be described.

Figure 18A:
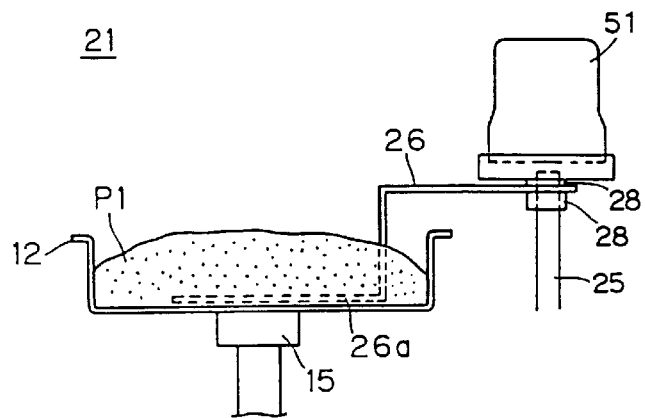
FIGS. 18A to 18C are diagrams illustrating how the measurement apparatus of FIG. 10 measures the spatula angle.

In FIG. 10, the guide 14, the table 13, and the shocker 41 are dismounted from the rectangular vat 12, and instead the spatula-angle measurement unit 21 is mounted. Next, the lifting motor 30 is rotated so that, by the action of the cam 31, the rectangular vat 12 is lifted up to a predetermined position near the spatula 26. Then, the powdery or granular material is fed from the vibration unit 4 and stacked onto the rectangular vat 12 to form thereon a pile P1 of the powdery or granular material as shown in FIG. 18A.

Figure 18B:
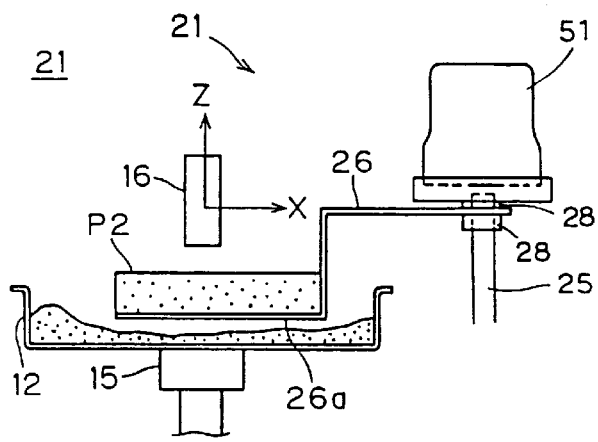
Figure 18C:
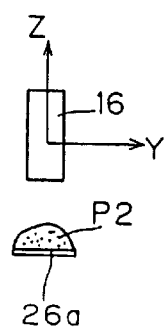

Next, the lifting motor 30 rotates so that, by the action of the cam 31, the rectangular vat 12 is moved downward. Then, as shown in FIGS. 18B and 18C, a pile P2 of the powdery or granular material is formed on the spatula 26. Note that FIG. 18C is a left side view of the spatula 26 shown in FIG. 18B. The sensor 16 is placed on the left-hand side in FIG. 18C, and emits sensor light in the Y direction. First, the sensor 16 is moved downward from above. Then, while the sensor is emitting sensor light toward the pile P2 of the powdery or granular material, it is moved in the Z direction by a predetermined distance a predetermined number of times so that, each time the sensor is so moved, measurement points are detected. From the data of the positions of those measurement points, an approximating straight line is calculated, and then the inclination angle (the spatula angle before collapse) of this approximating straight line with respect to a horizontal line is determined. To increase measurement accuracy, it is also possible to move the sensor 16 also in the X direction to measure the inclination angle more than once and calculate the average. Here, the approximating straight line is calculated by the same method as for the angle-of-repose measurement described earlier.

Next, by the action of the shocker 51 that has the same structure as the shocker 41 shown in FIG. 17, a shock is delivered to the spatula 26 to cause the pile P2 of the powdery or granular material to collapse, and thereafter, through the same procedure as described above, the spatula angle after collapse is measured, and the average of the spatula angles before and after collapse is calculated.

In the measurement apparatus of this embodiment, spatula-angle measurement can be performed by electrically controlling and thereby driving the lifting motor 30 for the rectangular vat 12 and the shocker 51. As a result, the entire sequence of operations starting with the lowering of the rectangular vat 12 and ending with the measurement of the spatula angle can be performed fully automatically. This helps reduce the time and effort required to conduct the measurement. Moreover, since it is possible to deliver a shock to the pile P of the powdery or granular material on the spatula 26 in a fixed manner, it is possible to measure the spatula angle after collapse with increased measurement accuracy.

Moreover, this embodiment employs a panel computer 19 that incorporates an operation unit to be operated by the user, a display unit for displaying the settings made and the operation underway, and a control unit for controlling the shocker 41, the actuator 18, and other components and for processing the measurement data. As a result, the measurement apparatus 101, despite being moderately sized, can be fitted with a large-screen operation/display unit that provides a graphical user interface as shown in FIGS. 19 to 22 without wasting available space so as to be easy to operate even for a first-time user.

Figure 23:
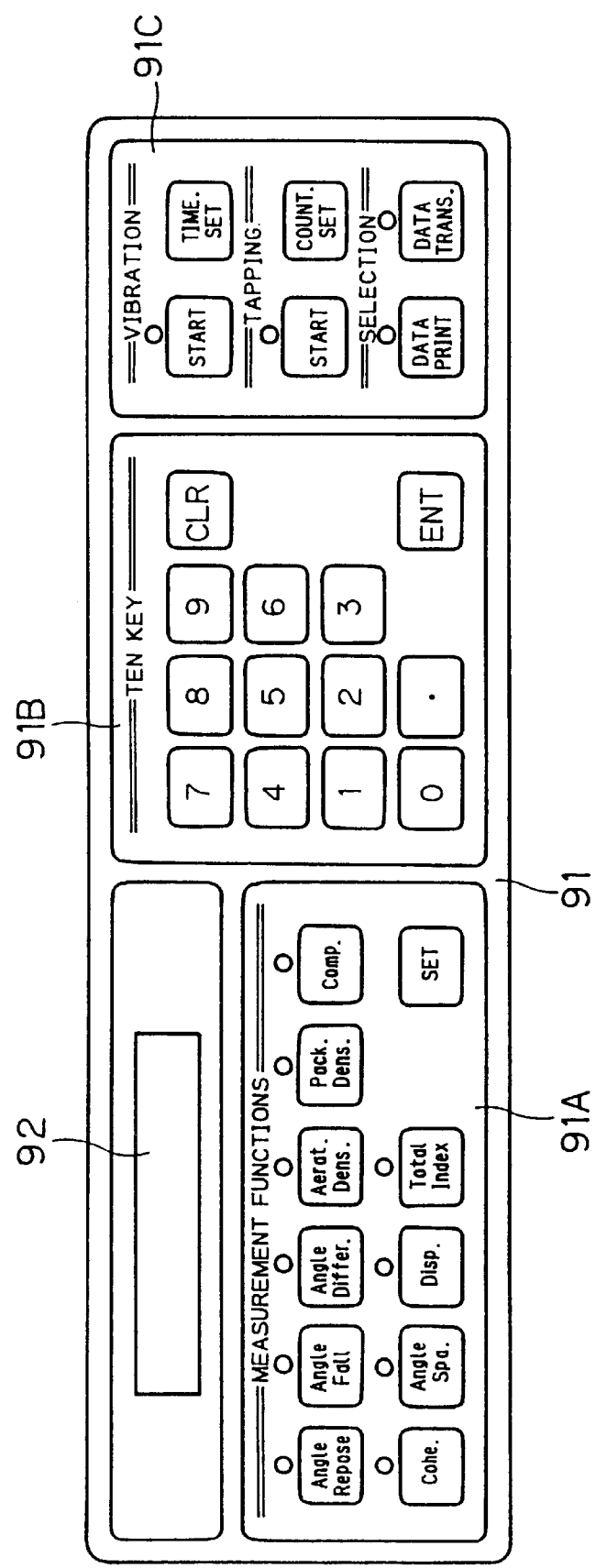
FIG. 23 is a plan view of the operation/display panel of the measurement apparatus of FIG. 1.

In the first embodiment, the computer has an operation/display unit as shown in FIG. 23. The user selects the type of measurement and others by the use of the function keys 91A provided on the operation unit 91, and, looking at the display unit 92, selects and enters measurement conditions and others by the use of the function keys 91A and the numerical keys 91B before starting measurement. In addition, where necessary, the user can request printing of data, starting of a tapping motor, stacking of the powdery or granular material, and others by the use of the control switches 91C.

The operation/display unit shown in FIG. 23 provides an interactive user interface. However, since this is a character-based user interface, it is necessary for the user to recognize and understand the labels, such as those indicating the measurement types, that appear on the unit before selecting or entering anything. Operating such an operation/display unit requires unduly much time. In particular, a first-time user, while conducting measurement, needs to consult the manual or the like incessantly for the terms appearing on the display unit 92 or for the position of the item the user wishes to choose, and thus tends to spend unduly much time to conduct measurement.

Figure 19:
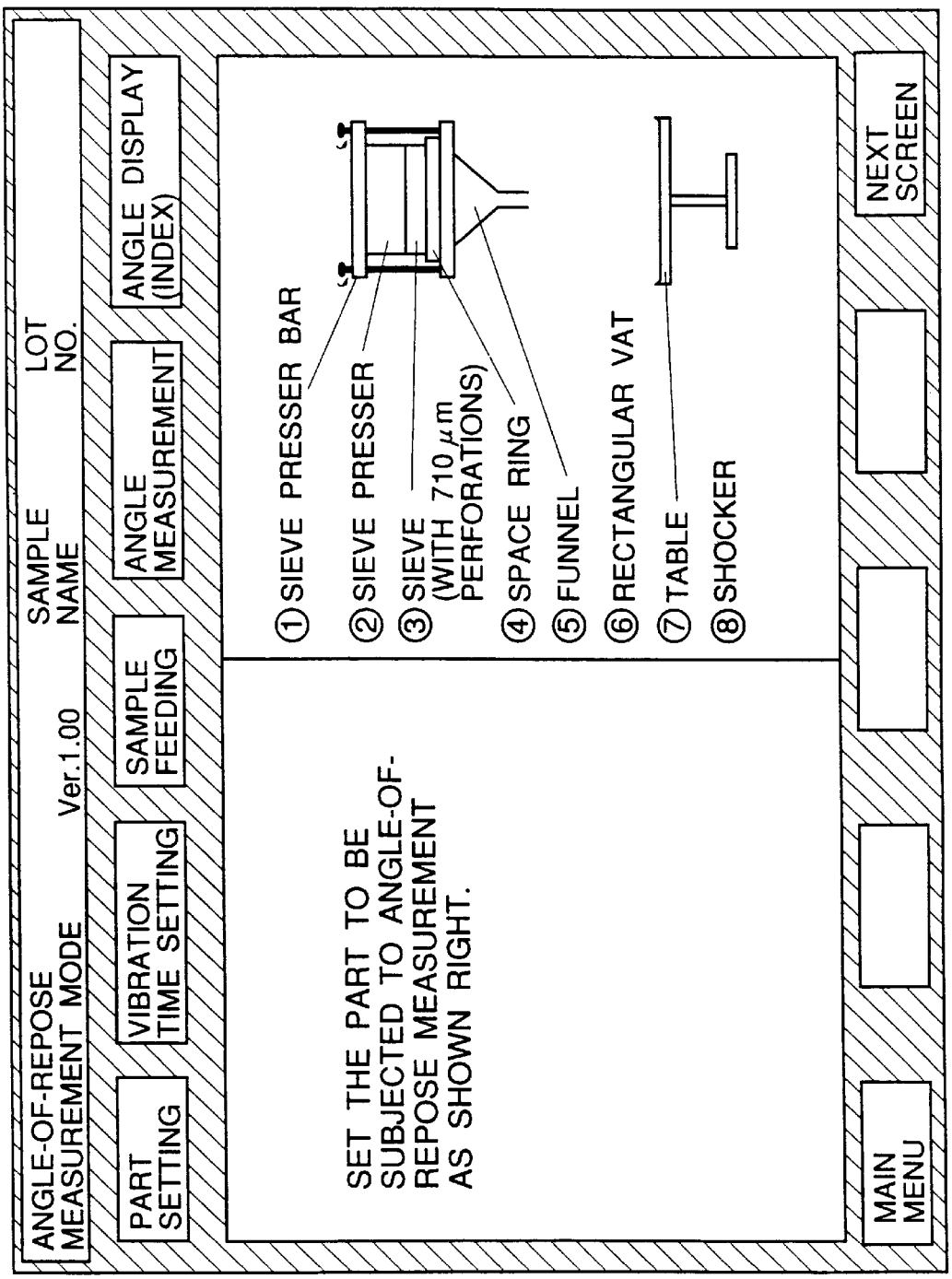
FIG. 19 is a diagram showing a display screen of the computer of the measurement apparatus of FIG. 10.
Figure 20:
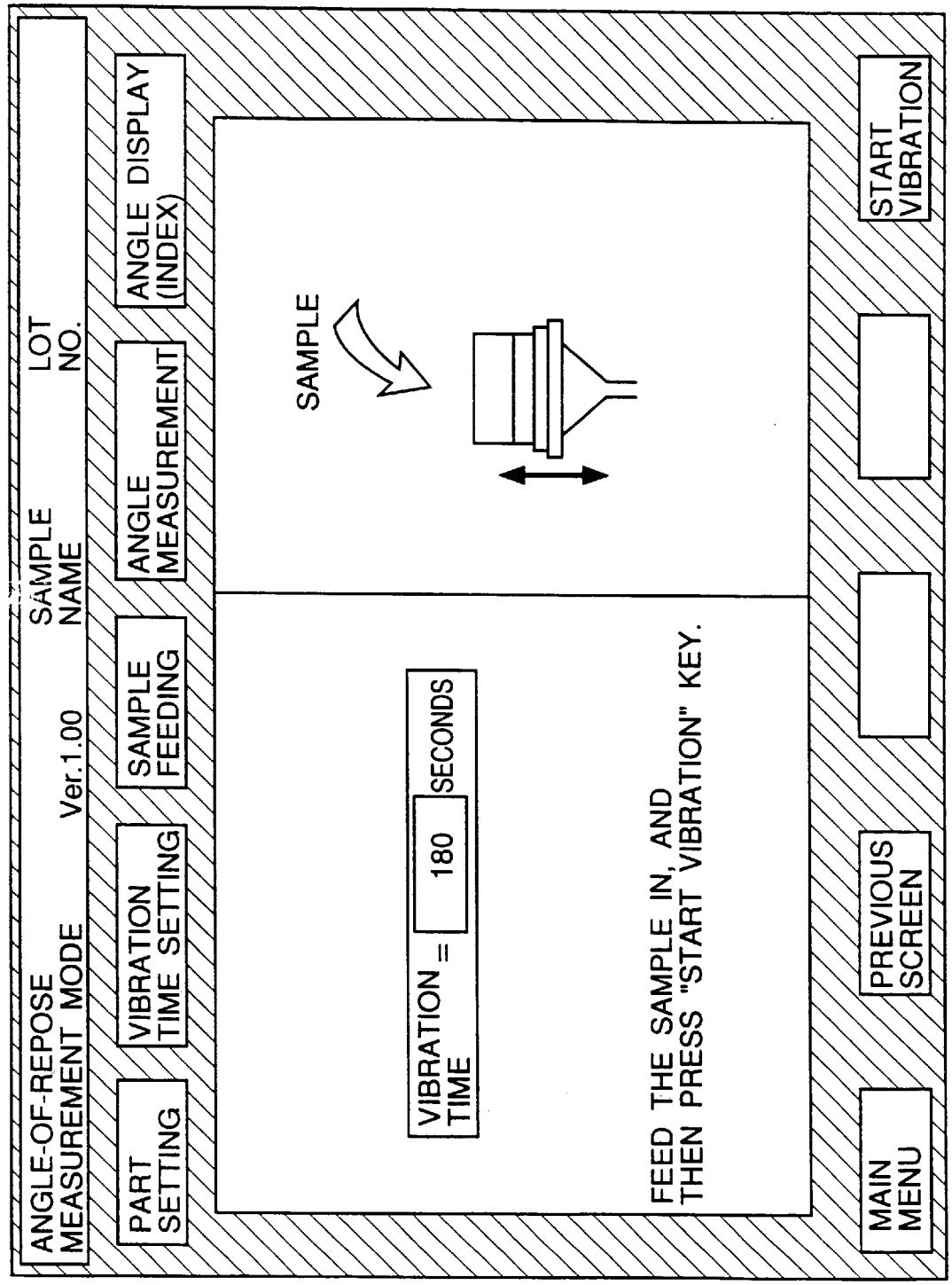
FIG. 20 is a diagram showing another display screen of the computer of the measurement apparatus of FIG. 10.
Figure 21:
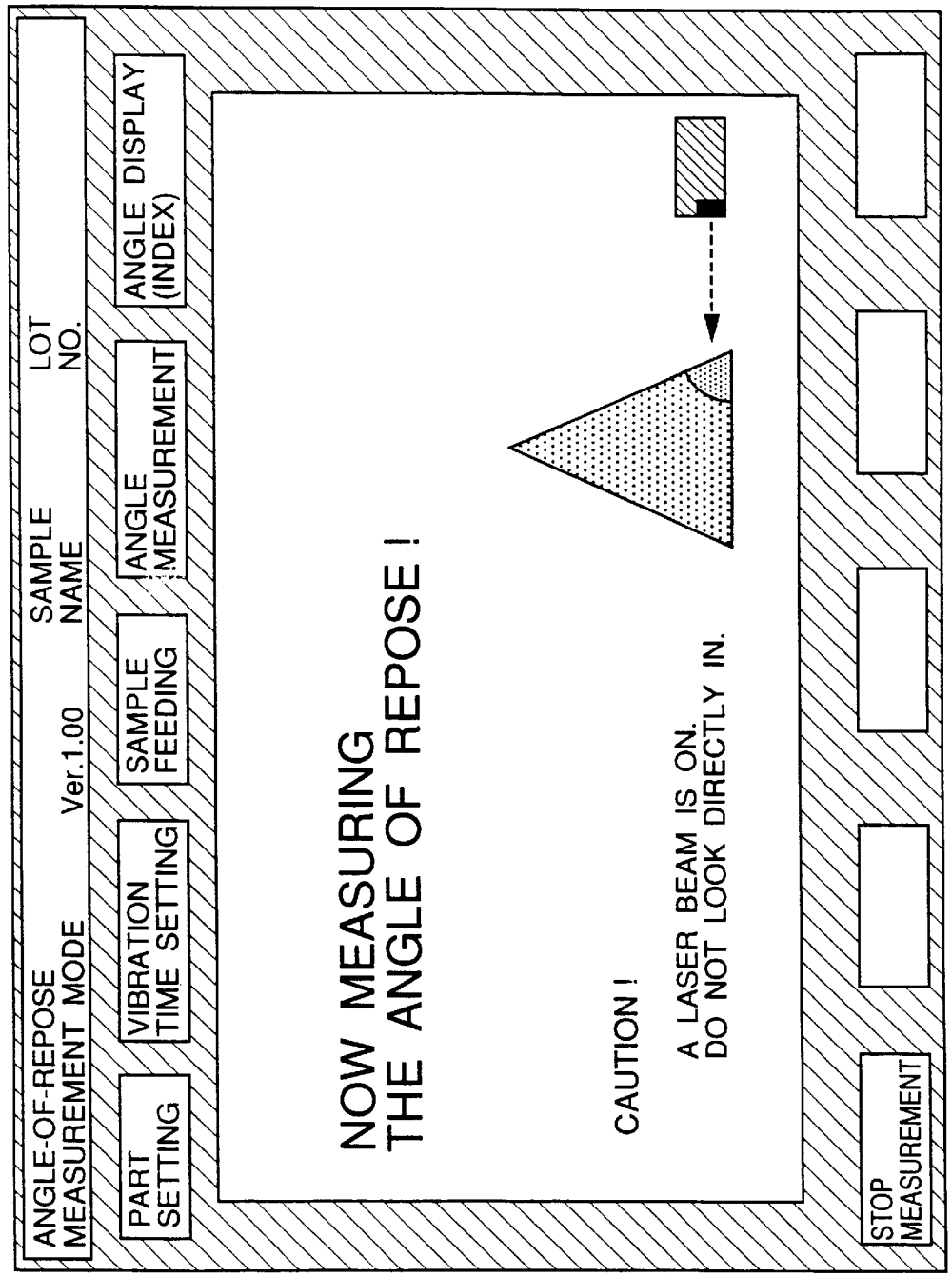
FIG. 21 is a diagram showing another display screen of the computer of the measurement apparatus of FIG. 10.
Figure 22:
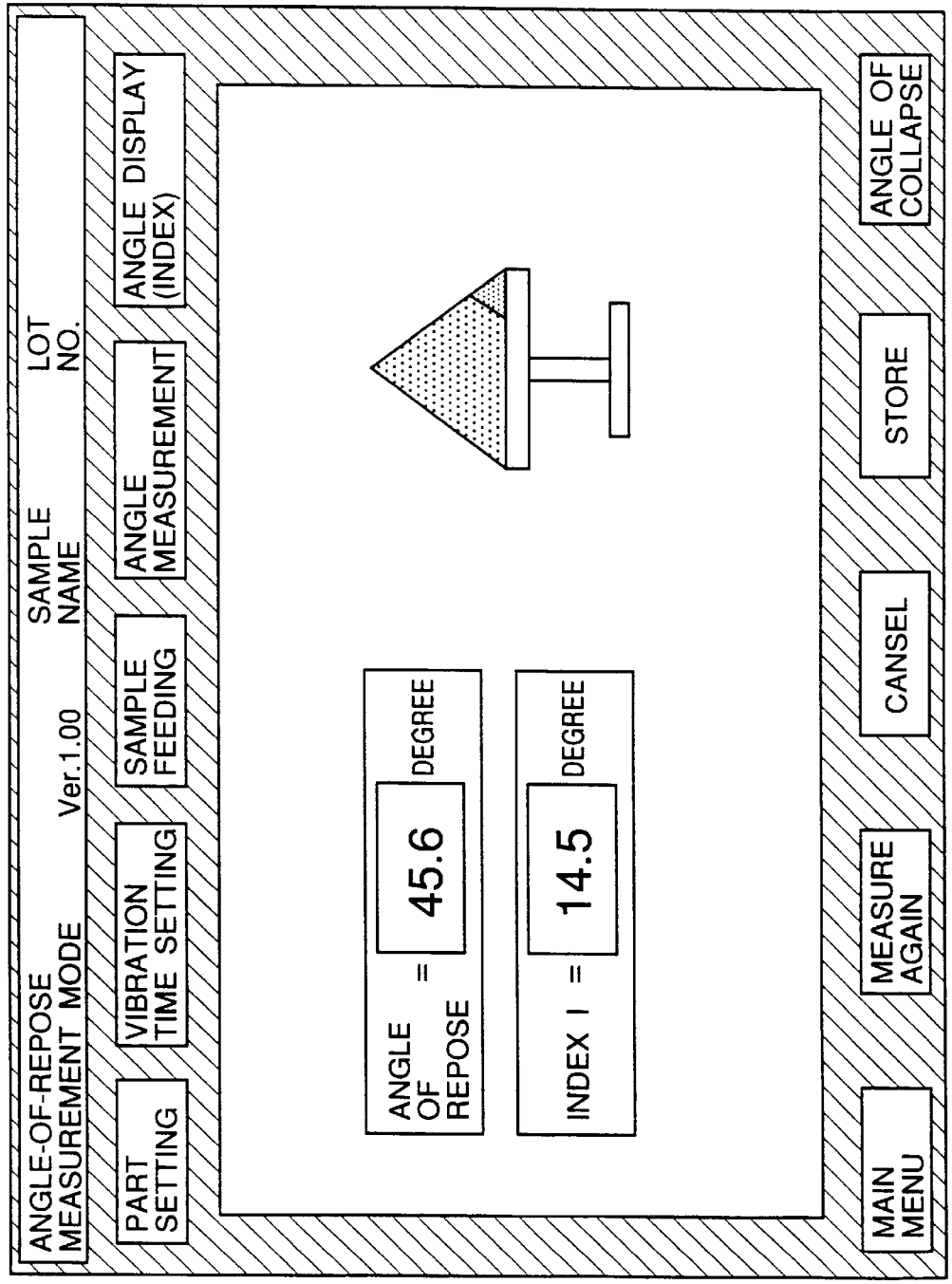
FIG. 22 is a diagram showing yet another display screen of the computer of the measurement apparatus of FIG. 10.

By contrast, in this embodiment, the panel-type computer displays points to be noted, instructions, and other information on the panel in an easy-to-follow way using diagrams and others so that the user can select the measurement type and measurement conditions based on judgments made visually by watching the panel before starting measurement. After measurement, measurement results such as the angle of repose and the angle of collapse are displayed on the panel. This ensures easy operation even for a first-time user, and makes it possible to perform measurement quickly. FIG. 19 shows a screen explaining how the necessary components are mounted, FIG. 20 shows a screen for setting conditions, FIG. 21 shows a screen for displaying a warning during measurement, and FIG. 22 shows a screen for displaying measurement results.

It is to be understood that the application of the present invention is not limited to the specific embodiments described heretofore, and that the present invention can be practiced in various manners within the scope of the appended claims.

What is claimed is:

1. A method of measuring the inclination angle of a pile of a powdery or granular material, comprising:

a first step of placing, by the side of a conical pile of the powdery or granular material stacked on a horizontal surface, a sensor that emits sensor light and, by receiving light reflected from a spot illuminated by the sensor light, measures a distance to that spot, said sensor being placed in such a way that an opening through which said sensor light is emitted faces a free surface of said pile of the powdery or granular material and that an optical axis of said sensor light runs in a horizontal direction;

a second step of moving said sensor in a horizontal direction perpendicular to said optical axis to detect a distance to each of a plurality of measurement points along a line that runs on said free surface so as to face a movement path of said sensor, said measurement points being arranged along said line at regular intervals in a horizontal direction, starting at one end and ending at the other end of said line in a horizontal direction;

a third step of moving said sensor in a vertical direction a predetermined distance at a time and performing said second step every time the sensor is so moved;

a fourth step of extracting a measurement point that is closest to said sensor in each session of said second step and determining a function describing a straight line approximating a curve through all of the thus extracted measurement points by a least-squares method; and a fifth step of determining an inclination angle of the straight line determined in said forth step with respect to a horizontal plane.

2. A method of measuring the inclination angle of a pile of a powdery or granular material, comprising:

a first step of placing, above a conical pile of the powdery or granular material stacked on a horizontal surface, a sensor that emits sensor light and, by receiving light reflected from a spot illuminated by the sensor light, measures a distance to that spot, said sensor being placed in such a way that an opening through which said sensor light is emitted faces a free surface of said pile of the powdery or granular material and that an optical axis of said sensor light runs in a vertical direction;

a second step of moving said sensor in a horizontal direction within a vertical plane including a vertex of said pile of the powdery or granular material to detect a distance to each of a plurality of measurement points along a ridge line of said pile of the powdery or granular material, said measurement points being arranged along said ridge line at regular intervals in a horizontal direction;

a third step of determining a function describing a straight line approximating a curve through said plurality of measurement points by a least-squares method; and a fourth step of determining an inclination angle of the straight line determined in said third step with respect to a horizontal plane.

3. A method of measuring the inclination angle of a pile of a powdery or granular material as claimed in claim 2, wherein said second to fourth steps are performed on each of two opposite sides of the vertex of said pile of the powdery or granular material to calculate an average of two inclination angles obtained.

4. A method of measuring the inclination angle of a pile of a powdery or granular material, comprising:

a first step of placing, by the side of a pile of the powdery or granular material stacked on a spatula supported horizontally, a sensor that emits sensor light and, by receiving light reflected from a spot illuminated by the sensor light, measures a distance to that spot, said sensor being placed in such a way that an opening through which said sensor light is emitted faces a free surface of said pile of the powdery or granular material and that an optical axis of said sensor light runs in a horizontal direction;

a second step of moving said sensor in a vertical direction to detect a distance to each of a plurality of measurement points along a line that runs on said free surface so as to face a movement path of said sensor, said measurement points being arranged along said line at regular intervals in a vertical direction;

a third step of determining a function describing a straight line approximating a curve through said plurality of measurement points by a least-squares method; and a fourth step of determining an angle of the straight line determined in said third step with respect to a horizontal plane.

5. A method of measuring the inclination angle of a pile of a powdery or granular material as claimed in claim 4, wherein said second to fourth steps are performed in each of a plurality of portions along a length of said spatula to calculate an average of a plurality of inclination angles obtained.

6. An apparatus for measuring the inclination angle of a pile of a powdery or granular material, comprising:

a horizontal surface on which the powdery or granular material is stacked in a pile;

a sensor, placed by the side of the powdery or granular material stacked in a conical pile on said horizontal surface, that emits sensor light in a horizontal direction toward a free surface of said pile of the powdery or granular material and, by receiving light reflected from a spot illuminated by said sensor light, detects a distance to that spot;

a moving means for moving said sensor in horizontal and vertical directions perpendicular to an optical axis of said sensor light; and a control means for controlling said moving means and for processing data obtained from said sensor, wherein said sensor is moved in a vertical direction a predetermined distance at a time and, every time said sensor is so moved, a step is performed in which said sensor is moved in a horizontal direction to detect a distance to each of a plurality of measurement points along a line that runs on the free surface of said pile of the powdery or granular material so as to face a movement path of said sensor, with said measurement points arranged along said line at regular intervals in a horizontal direction, starting at one end and ending at the other end of said line in a horizontal direction, so that a measurement point that is closest to said sensor is extracted in each session of said step and a function describing a straight line approximating a curve through all of the thus extracted measurement points is determined by a least-squares method in order to determine an angle of the thus determined straight line with respect to a horizontal plane.

7. An apparatus for measuring the inclination angle of a pile of a powdery or granular material, comprising:

a horizontal surface on which the powdery or granular material is stacked in a pile;

a sensor, placed above the powdery or granular material stacked in a conical pile on said horizontal surface, that emits sensor light in a vertical direction toward a free surface of said pile of the powdery or granular material and, by receiving light reflected from a spot illuminated by said sensor light, detects a distance to that spot;

a moving means for moving said sensor in a horizontal direction within a vertical plane including a vertex of said pile of the powdery or granular material; and a control means for controlling said moving means and for processing data obtained from said sensor, wherein said sensor is moved in a horizontal direction to detect a distance to each of a plurality of measurement points along a ridge line of said pile of the powdery or granular material, with said measurement points arranged along said ridge line at regular intervals in a horizontal direction, so that a function describing a straight line approximating a curve through those measurement points is determined by a least-squares method in order to determine an angle of the thus determined straight line with respect to a horizontal plane.

8. An apparatus for measuring the inclination angle of a pile of a powdery or granular material as claimed in claim 7, wherein the step in which said sensor is moved in a horizontal direction to detect a distance to each of a plurality of measurement points along a ridge line of said pile of the powdery or granular material, with said measurement points arranged along said ridge line at regular intervals in a horizontal direction, so that a function describing a straight line approximating a curve through those measurement points is determined by a least-squares method in order to determine an angle of the thus determined straight line with respect to a horizontal plane is performed on each of two opposite sides of the vertex of said pile of the powdery or granular material to calculate an average of two inclination angles obtained.

9. An apparatus for measuring the inclination angle of a pile of a powdery or granular material, comprising:

a spatula supported horizontally;

a sensor, placed by the side of a pile of the powdery or granular material stacked on said spatula, that emits sensor light in a horizontal direction toward a free surface of said pile of the powdery or granular material and, by receiving light reflected from a spot illuminated by said sensor light, detects a distance to that spot;

a moving means for moving said sensor in a vertical direction; and a control means for controlling said moving means and for processing data obtained from said sensor, wherein said sensor is moved in a vertical direction to detect a distance to each of a plurality of measurement points along a line that runs on said free surface so as to face a movement path of said sensor, with said measurement points being arranged along said line at regular intervals in a vertical direction, so that a function describing a straight line approximating a curve through those measurement points is determined by a least-squares method in order to determine an angle of the thus determined straight line with respect to a horizontal plane.

10. An apparatus for measuring the inclination angle of a pile of a powdery or granular material as claimed in claim 9, wherein said sensor is movable along a length of said spatula so that the step in which said sensor is moved in a vertical direction to detect a distance to each of a plurality of measurement points along a line that runs on said free surface so as to face a movement path of said sensor, with said measurement points being arranged along said line at regular intervals in a vertical direction, so that a function describing a straight line approximating a curve through those measurement points is determined by a least-squares method in order to determine an angle of the thus determined straight line with respect to a horizontal plane is performed in each of a plurality of portions along the length of said spatula to calculate an average of a plurality of inclination angles obtained.

11. A method of measuring the inclination angle of a pile of a powdery or granular material, comprising:

a first step of placing a sensor that emits sensor light toward the powdery or granular material stacked in a conical pile on a horizontal surface and, by receiving light reflected from a spot illuminated by said sensor light, detects a distance to said pile of the powdery or granular material in a measurement start position in which said sensor light illuminates an arbitrary spot on said pile of the powdery or granular material from a first direction that is not vertical;

a second step of, within at least one plane that exists between said arbitrary spot and a vertex of said pile of the powdery or granular material and that is parallel to said first direction and parallel to a second direction perpendicular to said first direction, moving said sensor light in said second direction while measuring a distance from said sensor to said pile of the powdery or granular material in order to find a point on said pile of the powdery or granular material at which said distance is smallest;

a third step of, within a vertical plane that includes a point selected from the thus found smallest-distance points and that is parallel to said first direction, moving said sensor light in a direction perpendicular to said first direction to detect a plurality of measurement points on said pile of the powdery or granular material; and a fourth step of determining an angle, with respect to a horizontal plane, of a straight line obtained by approximation from positions of said plurality of measurement points.

12. A method of measuring the inclination angle of a pile of a powdery or granular material as claimed in claim 11, wherein said sensor light is shone onto a point on a line that intersects, above said pile of the powdery or granular material, with an axis substantially through the center of said horizontal plane, and, from that point, said sensor light is moved downward until said pile of the powdery and granular material starts to be illuminated by said sensor light so that the position of said sensor at that moment is used as said measurement start position.

13. An apparatus for measuring the inclination angle of a pile of a powdery or granular material, comprising:

a table having a horizontal surface;

a sensor, placed by the side of the powdery or granular material stacked in a conical pile on the horizontal surface of said table, that emits sensor light in a substantially horizontal first direction toward said pile of the powdery or granular material and, by receiving light reflected from a spot illuminated by said sensor light, detects a distance to said pile of the powdery or granular material;

a moving means for moving said sensor in a second direction that is horizontal and perpendicular to said first direction and in a third direction that is perpendicular to said first direction within a vertical plane including an optical axis of said sensor light; and a control means for controlling said moving means and for processing data obtained form said sensor, wherein, after said sensor is placed in a measurement start position in which said sensor light illuminates a point on said pile of the powdery and granular material, a first step in which said sensor is moved in said second direction a predetermined distance at a time within a substantially horizontal plane and, every time said sensor is so moved, a position of a point on said pile of the powdery or granular material that is illuminated by said sensor light is detected to find a point on said pile of the powdery or granular material at which a distance from said sensor to said pile of the powdery or granular material within said substantially horizontal plane is smallest, a second step in which said first step is performed every time said sensor is moved in said third direction a predetermined distance at a time, a third step in which a position in said second direction of said sensor is made to coincide with a position in said second direction of a point selected from the smallest-distance points found in said second step as points at which a distance from said sensor to said pile of the powdery or granular material within said substantially horizontal plane is smallest and, every time said sensor is moved in said third direction a predetermined distance at a time, a position of a measurement point on said pile of the powdery or granular material that is illuminated by said sensor light is detected, and a fourth step in which a straight line is determined by approximation from data of positions of a plurality of measurement points detected in said third step in order to determine an angle of said straight line with respect to a horizontal plane are performed.

14. An apparatus for measuring the inclination angle of a pile of a powdery or granular material as claimed in claim 13, wherein said control means is realized as a panel-type computer that displays interactive screens on a panel and that performs processing and changes screens in response to operations by a user.

15. An apparatus for measuring the inclination angle of a pile of a powdery or granular material as claimed in claim 13, wherein said sensor is, in said second direction, positioned in a predetermined position relative to a center of said table and, in said third direction, positioned a predetermined distance above said pile of the powdery or granular material, and said sensor is moved downward while emitting said sensor light so that a position of said sensor at which said pile of the powdery or granular material starts to be illuminated by said sensor light is used as said measurement start position.

16. An apparatus for measuring the inclination angle of a pile of a powdery or granular material as claimed in claim 13, further comprising:

a shocker having a base joined to said table, an electromagnet placed above said base, and a weight placed so as to be movable vertically between said base and said electromagnet and made at least partially of a magnetic material, wherein, when said electromagnet is fed with an electric current, said weight is attracted to said electromagnet and, when the electric current to said electromagnet is cut off, said weight drops onto said base and thereby delivers a shock to said table.

17. An apparatus for measuring the inclination angle of a pile of a powdery or granular material as claimed in claim 13, further comprising:

a funnel for letting the powdery or granular material fall substantially to a center of said table from above to form a pile of the powdery or granular material thereon;

a base plate having a through hole of a diameter smaller than a maximum diameter of said funnel for supporting said funnel by means of said through hole; and a ring member positioned on said base plate and having a bore that engages with that portion of said funnel at which said funnel has a largest diameter, wherein said funnel is positioned on said base plate by means of said bore formed in said ring member.

18. An apparatus for measuring the inclination angle of a pile of a powdery or granular material, comprising:

a spatula having a sample stage with a rectangular upper surface;

a vat, placed below said spatula, on which the powdery or granular material is stacked in a pile;

a first moving means for moving said vat vertically;

a sensor that emits sensor light in a first direction perpendicular to a direction of a length of said spatula and, by receiving light reflected from a spot illuminated by said sensor light on the pile of the powdery or granular material stacked on said sample stage, detects a distance to said pile of the powdery or granular material;

a second moving means for moving said sensor in the direction of the length of said spatula and in a second direction perpendicular both to said direction of the length of said spatula and to said first direction;

a shocker having a base joined to said spatula, an electromagnet placed above said base integrally therewith, and a weight placed so as to be vertically movable between said base and said electromagnet and made at least partially of a magnetic material, said weight being attracted to said electromagnet when said electromagnet is fed with an electric current, said weight dropping onto said base to deliver a shock to said spatula when the electric current to said electromagnet is cut off; and a control means for controlling said first and second moving means and said shocker and for processing data obtained from said sensor, wherein said control means automatically controls and performs in predetermined order a predetermined number of times a first step in which said vat placed near said spatula and stacked with the pile of the powdery or granular material is moved downward, a second step of, every time said sensor is moved to a predetermined position, detecting a position of a point on said pile of the powdery or granular material that is illuminated by said sensor light, a third step of delivering a shock to said spatula by means of said shocker, and a fourth step of determining a spatula angle of said pile of the powdery or granular material from data of a plurality of positions obtained in the second step.

19. An apparatus for measuring the inclination angle of a pile of a powdery or granular material as claimed in claim 18, wherein said control means is realized as a panel-type computer that displays interactive screens on a panel and that performs processing and changes screens in response to operations by a user.

* * * * *